United States Patent [19]
Gorman et al.

[11] Patent Number: 5,968,509
[45] Date of Patent: Oct. 19, 1999

[54] ANTIBODIES WITH BINDING AFFINITY FOR THE CD3 ANTIGEN

[75] Inventors: Scott David Gorman, Great Shelford; Edward Graham Routledge; Herman Waldmann, both of Cambridge, all of United Kingdom

[73] Assignee: BTP International Limited, London, United Kingdom

[21] Appl. No.: 08/362,780

[22] Filed: Dec. 23, 1994

Related U.S. Application Data

[63] Continuation of application No. 07/862,543, Jun. 23, 1992, abandoned.

[30] Foreign Application Priority Data

Oct. 5, 1990 [GB] United Kingdom .................. 9021679

[51] Int. Cl.$^6$ .................. A61K 39/395; C07K 16/28
[52] U.S. Cl. .................. 424/133.1; 424/142.1; 424/154.1; 530/387.3; 530/388.75
[58] Field of Search .................. 424/133.1, 142.1, 424/154.1, 183.1; 435/69.6, 69.7, 70.21, 172.2, 172.3, 328, 343.2, 252.3, 252.33, 320.1, 449, 451, 452, 454, 455; 530/387.3, 388.75, 389.6, 391.7

[56] References Cited

U.S. PATENT DOCUMENTS 5,225,539  7/1993  Winter .................................. 530/387.3

OTHER PUBLICATIONS

Routledge et al. "A humanized monovalent CD3 antibody . . . " Eur. J. Immunol. 21 (1991) pp. 2649–2898.
Clark et al. "The Improved lytic function . . . " Euro. Jour. Immunol. 1989, 19: 381–388.
Rudikoff et al. "Single amino acid . . . " Proc. Natl Acad. of Sci. USA 79:1979–1983. Mar. 1982.
Riechmann et al. "Reshaping human antibodies . . . " Nature 332: 323–377, Mar. 24, 1988.
Verhoeyen et al. "Reshaping human antibodies . . . " Science 239:1534–1536, Mar. 25, 1988.
Queen et al. "A humanized antibody . . . " Proc. Natl Aca. Sci. USA, 86:10029–10033, Dec. 1989.
Cobbold et al. "Therapeutic potential of . . . " Nature 308:460–462, Mar. 29, 1984.
Osband et al. "Problems on the investigational study . . . " Immunology Today 11(6):193–195, 1990.
Waldmann "Monoclonal antibodies in diagnosis and therapy" Science, vol. 252:1657–1662, Jun. 21, 1991.
Dillman, R.O. "Monoclonal antibodies for treating cancer" Annals of Internal Medicine 1989 111:592–603.
Hird et al. "Immunotherapy with monoclonal antibodies" Genes and Cancer, pp. 183–189. Carey et al. Eds. Wiley & Sons Ltd. 1990.

*Primary Examiner*—Robert D. Budens
*Attorney, Agent, or Firm*—Nixon & Vanderhye

[57] ABSTRACT

An antibody or antibody fragment with a binding affinity for the CD3 antigen, having a human constant region, and human or rat variable framework region, a heavy chain with CDRs having the amino acid sequences:

(a) Ser-Phe-Pro-Met-Ala (SEQ ID NO:1),
(b) Thr-Ile-Ser-The-Ser-Gly-Gly-Arg-Thr-Tyr-Tyr-Arg-Asp-Ser-Val-Lys-Gly (SEQ ID NO:2),
(c) Phe-Arg-Gln-Tyr-Ser-Gly-Gly-Phe-Asp-Tyr (SEQ ID NO:3), and light chain with CDRs having the amino acid sequences:

(d) Thr-Leu-Ser-Ser-Gly-Asn-Ile-Glu-Asn-Tyr-Val-His (SEQ ID NO:4),
(e) Asp-Asp-Asp-Lys-Arg-Pro-Asp (SEQ ID NO:5),
(f) His-Ser-Tyr-Val-Ser-Ser-Phe-Asn-Val (SEQ ID NO:6), in which the heavy chain CDRs are arranged in the order (a), (b), (c) in the leader→constant region direction and the light chain CDRs are arranged in the order (d), (e), (f) in the leader→constant region direction.

7 Claims, 11 Drawing Sheets

ANTIBODIES WITH BINDING AFFINITY FOR THE CD3 ANTIGEN

This is a Rule 60 continuation of application Ser. No. 07/862,543, filed Jun. 23, 1992, now abandoned.

This invention relates to antibodies, in particular to re-shaped antibodies directed against the CD3 antigen on the surface of human T-cells.

Antibodies, or immunoglobulins, comprise two heavy chains linked together by disulphide bonds and two light chains, each light chain being linked to a respective heavy chain by disulphide bonds in a "Y" shaped configuration. The two "arms" of the antibody are responsible for antigen binding, having regions where the polypeptide structure varies, and are termed Fab' fragments (fragment-antigen-binding) or F(ab')₂ which represents two Fab' arms linked together by disulphide bonds. The "tail" or central axis of the antibody contains a fixed or constant sequence of peptides and is termed the Fc fragment (fragment-crystalline). The production of monoclonal antibodies was first disclosed by Kohler and Milstein (Kohler & Milstein, Nature, 256, 495–497 (1975)). Such monoclonal antibodies have found widespread use as diagnostic agents and also in therapy.

Each heavy chain has at one end a variable domain followed by a number of constant domains. Each light chain has a variable domain at one end and a constant domain at its other end, the light chain variable domain being aligned with the variable domain of the heavy chain and the light chain constant domain being aligned with the first constant domain of the heavy chain (CH1). The constant domains in the light and heavy chains are not involved directly in binding the antibody to antigen. The light chain constant region and the CH1 region of the heavy chain account for 50% of each Fab' fragment.

The variable domains of each pair of light and heavy chains form the antigen binding site. The domains on the light and heavy chains have the same general structure and each domain comprises four framework regions, whose sequences are relatively conserved, connected by three complementarity determining regions (CDRs) (Kabat et al, Sequences of Proteins of Immunological Interest, U.S. Department of Health and Human Services (1987)). The four framework regions largely adopt a beta-sheet conformation and the CDRs form loops connecting, and in some cases forming part of, the beta-sheet structure. The CDRs are held in close proximity by the framework regions and, with the CDRs from the other domain, contribute to the formation of the antigen binding site.

In recent years, molecular biology techniques have allowed the production of a wide range of heterologous polypeptides by transformation of host cells with DNA sequences coding for the desired polypeptide. Immunoglobulin polypeptides have been produced by recombinant DNA techniques, see for example EP-A-0 088 994 (Schering Corporation), EP-A-1 102 634 (Takeda Chemical Industries Ltd.) and EP-A-0 125 023 (Genentech Inc.). These techniques have also allowed the stable introduction of immunoglobulin genes into myeloma cells.

When murine or rat monoclonal antibodies or even part human chimeric antibodies (antibodies where the antigen binding portion of an immunoglobulin is attached to at least part of another protein by a peptide linkage) comprising a mouse or rat variable domain is injected into a human in therapy, the human body's immune system could recognise that variable domain as foreign and thus produce an immune response. Hence, upon repeated injections of the mouse or rat monoclonal or chimeric antibody into humans, the effectiveness would be lost or reduced by the reaction of the body's immune system against the foreign antibody.

EP-A-0 239 400 (Winter) describes a monoclonal antibody in which only the CDRs of the antibody will be foreign to the body in order to minimise side effects due to its antigenicity if used for human therapy. Although, for example, human, mouse and rat framework regions have characteristic sequences, there seem to be no characteristic features which distinguish human from mouse and rat CDRs. Thus, an antibody comprised of mouse or rat CDRs in a human framework may well be no more foreign to the body than a genuine human antibody.

It is not clear however that the method of "humanizing" antibodies described in the above application will be suitable for application as a general method to all antibodies. Antibodies have either kappa or lambda light chains and one of alpha, mu, gamma, epsilon or delta heavy chains, specific combinations of which may make the above method of humanising antibodies inapplicable.

Until now, all of the humanised antibodies have contained a light chain of the kappa type. However, it has now been found possible to humanise an antibody directed against the human T-cell CD3 antigen (the monoclonal antibody secreted by the rat hybridoma YTH12.5.14.2 hereinafter referred to as YTH12.5), even though the antibody has a lambda type light chain. The presence of the lambda light chain required a different approach from that used for the humanisation of the mouse monoclonal antibody as described in EP-A-0 239 400.

Accordingly the present invention comprises a ligand with a binding affinity for the CD3 antigen having at least one CDR which is of different origin to the variable framework regions and/or constant regions of the ligand, the at least one CDR being selected from the amino acid sequences:

(a) Ser-Phe-Pro-Met-Ala, (Sequence ID No: 1)
(b) Thr-Ile-Ser-Thr-Ser-Gly-Gly-Arg-Thr-Tyr-Tyr-Arg-Asp-Ser-Val-Lys-Gly, (Sequence ID No: 2)
(c) Phe-Arg-Gln-Tyr-Ser-Gly-Gly-Phe-Asp-Tyr, (Sequence ID No: 3)
(d) Thr-Leu-Ser-Ser-Gly-Asn-Ile-Glu-Asn-Asn-Tyr-Val-His, (Sequence ID No: 4)
(e) Asp-Asp-Asp-Lys-Arg-Pro-Asp, (Sequence ID No: 5)
(f) His-Ser-Tyr-Val-Ser-Ser-Phe-Asn-Val, (Sequence ID No: 6)

and conservatively modified variants thereof.

The term "conservatively modified variants" is one well known in the art and indicates variants containing changes which are substantially without effect on antibody-antigen affinity.

The CDRs of the invention are situated within framework regions of the heavy chain (for (a), (b) and (c)) and light chain (for (d), (e) and (f)) variable domains. Moreover, in many but not all cases the ligand will also comprise a constant region. It is possible for the at least one CDR to be of the same origin as its variable framework region but of a different origin from the constant region, for example in a part human chimeric antibody. However, more commonly the at least one CDR will be of different origin from the variable framework regions, for example in a single domain ligand which does not contain a constant region as discussed hereinafter, and usually also of different origin from the constant region where one is present, for example in an antibody or fragment thereof.

Ligands according to the invention may contain varying numbers of CDRs. Thus, for example, the entities known as molecular recognition units contain a single CDR, but of rather greater interest among ligands which do not contain both a heavy and light chain are the single domain ligands described in European Patent Application No. 0 368 684 which contain three CDRs.

In a preferred embodiment of the invention, therefore, the ligand has three CDRs corresponding to the amino acid sequences (a), (b) and (c) above or conservatively modified variants thereof and/or three CDRs corresponding to amino acid sequences (d), (e) and (f) or conservatively modified variants thereof, the heavy chain CDRs (a), (b) and (c) being of most importance.

The present invention is however of particular interest in relation to whole antibodies or fragments thereof containing both heavy and light chain variable regions. Thus the ligand of the invention preferably has the form of an antibody or fragment thereof with a binding affinity for the CD3 antigen having a heavy chain with at least one CDR selected from the amino acid sequences having the Sequence ID Numbers 1, 2 or 3 and conservatively modified variants thereof, and/or a light chain with at least one CDR selected from the amino acid sequences having the Sequence ID numbers 4, 5 or 6 and conservatively modified variants thereof.

Although as indicated hereinbefore, ligands according to the invention do not have to contain both one or more of the specified heavy chain CDRs and one or more of the specified light chain CDRs, the antibodies or fragments thereof will usually do so. The CDRs (a), (b) and (c) are arranged in the rat hybridoma YTH12.5 heavy chain in the sequence: framework region 1/(a)/framework region 2/(b)/framework region 3/(c)/framework region 4 in a leader→constant region direction and the CDRs (d), (e) and (f) are arranged in the hybridoma light chain in the sequence: framework region 1/(d)/framework region 2/(e)/framework region 3/(f)/framework region 4 in a leader→constant region direction. It is preferred, therefore, that where all three are present the heavy chain CDRs are arranged in the sequence (a), (b), (c) in a leader→constant region direction and the light chain CDRs are arranged in the sequence (d), (e), (f) in a leader→constant region direction.

It should be appreciated that it may be possible to have heavy chains and particularly light chains containing only one or two of the CDRs (a), (b) and (c) and (d), (e) and (f), respectively. However, although the presence of all six CDRs defined above is therefore not necessarily required in an antibody or fragment thereof according to the present invention, all six CDRs will most usually be present. A particularly preferred antibody or fragment thereof therefore has a heavy chain with three CDRs comprising the amino acid sequences (a), (b) and (c) or conservatively modified variants thereof and a light chain with three CDRs comprising the amino acid sequences (d), (e) and (f) or conservatively modified variants thereof in which the heavy chain CDRs are arranged in the order (a), (b), (c) in the leader constant region direction and the light chain CDRs are arranged in the order (d), (e), (f) in the leader constant region direction.

The invention may be applied to antibodies having a "Y" shaped configuration which have two identical light and two identical heavy chains and are thus bivalent with each antigen binding site having an affinity for the CD3 antigen. Alternatively, Fab' or F(ab')$_2$ fragments retaining the CDRs may be prepared. The invention is also applicable to antibodies and, where appropriate, fragments thereof, in which only one of the arms of the antibody has a binding affinity for the CD3 antigen. Such antibodies may take various forms. Thus the other arm of the antibody may have a binding affinity for an antigen other than CD3 so that the antibody is a bispecific antibody, for example as described in U.S. Pat. No. 4,474,893 and European Patent Applications Nos. 87907123.1 and 87907124.9. Alternatively, the antibody may have only one arm which exhibits a binding affinity, such an antibody being termed "monovalent".

Monovalent antibodies (or antibody fragments) may be prepared in a number of ways. Glennie and Stevenson (Nature, 295, 712–713, (1982)) describe a method of preparing monovalent antibodies by enzymic digestion. Stevenson et al. describe a second approach to monovalent antibody preparation in which enzymatically produced Fab' and Fc fragments are chemically cross-linked (Anticancer Drug Design, 3, 219–230 (1989)). In these methods the resulting monovalent antibodies have lost one of their Fab' arms. A third method of preparing monovalent antibodies is described in European Patent No. 131424. In this approach the "Y" shape of the antibody is maintained, but only one of the two Fab' domains will bind to the antigen. This is achieved by introducing into the hybridoma a gene coding for an irrelevant light chain which will combine with the heavy chain of the antibody to produce a mixture of products in which the monovalent antibody is the one of interest.

More preferably, however, the monovalent CD3 antibodies of the invention are prepared by a new method. This involves the introduction into a suitable expression system, for example a cell system as described hereinafter, together with genes coding for the heavy and light chains, of a gene coding for a truncated heavy chain in which the variable region domain and first constant region domain of the heavy chain are absent, the gene lacking the exon for each of these domains. This results in the production by the cell system of a mixture of (a) antibodies which are complete bivalent antibodies, (b) antibody fragments consisting only of two truncated heavy chains (i.e. an Fc fragment) and (c) fragments of antibody which are monovalent for the CD3 antigen, consisting of a truncated heavy chain and a light chain in association with the normal heavy chain. Such an antibody fragment (c) is monovalent since it has any only one Fab' arm. Production of a monovalent antibody in the form of such a fragment by this method is preferred for a number of reasons. Thus, the resulting antibody fragment is easy to purify from a mixture of antibodies produced by the cell system since, for example, it may be separable simply on the basis of its molecular weight. This is not possible in the method of European Patent No. 131424 where the monovalent antibody produced has similar characteristics to a bivalent antibody in its size and outward appearance. Additionally, the production of a monovalent antibody fragment by the new method uses conditions which can more easily be controlled and is thus not as haphazard as an enzyme digestion/chemical coupling procedure which requires the separation of a complex reaction product, with the additional advantage that the cell line used will continue to produce monovalent antibody fragments, without the need for continuous synthesis procedures as required in the enzyme digestion/chemical coupling procedure.

As indicated, the procedure just described for the preparation of monovalent antibody fragments is new and it may be applied to the production of antibody fragments in which the single binding affinity is for other than the CD3 antigen. Accordingly the present invention includes a process for the preparation of a monovalent antibody fragment which comprises culturing an expression system containing genes coding for the antibody heavy and light chains and a gene coding for a truncated heavy chain in which the variable domain and first constant region domain are absent to thereby effect expression of an antibody fragment possessing only one Fab' domain per Fc domain.

The CDRs of the invention are obtained from a rat CD3 antibody. Accordingly, although the variable domain framework regions can take various forms, they are preferably derived from rat or human antibodies. One possibility is for the ligand to have variable domain frameworks corresponding to that in the YT12.5 hybridoma although the constant region will then necessarily differ from that of this hybridoma. However the antibody of the invention is preferably in the humanised form as regards both the variable domain frameworks and as discussed hereinafter, the constant region.

Accordingly, the invention further comprises a ligand or an antibody or a fragment thereof in which the CDR or CDRs are combined with variable domain framework regions of or derived from those of human origin. Certain human variable domain framework sequences will be preferable for the grafting of the CDR sequences according to the invention, since the 3-dimensional conformation of the CDRs will be better maintained in such sequences and the antibody will retain a high level of binding affinity for the antigen. Desirable characteristics in such variable domain frameworks are the presence of key amino acids which maintain the structure of the CDR loops in order to ensure the affinity and specificity of the antibody for the CD3 antigen, the lambda type being preferred for the light chain.

We have identified human variable region frameworks which are particularly suitable for use in conjunction with the CDRs of the present invention. The heavy chain variable (V) region frameworks are those coded for by the human VH type III gene VH26.D.J. which is from the B cell hybridoma cell line 18/2 (Genbank Code: Huminghat, Dersimonian et al., Journal of Immunology, 139, 2496–2501). The light chain variable region frameworks are those of the human $V_L\lambda$ type VI gene SUT (Swissprot code; LV6CSHum, Solomon et al. In Glenner et al (Eds), Amyloidosis, Plenum Press N.Y., 1986, p.449. The one or more CDRs of th heavy chain of the rat anti-CD3 antibody are therefore preferably present in a human variable domain framework which has the following amino acid sequence reading in the leader→constant region direction, CDR indicating a CDR (a), (b) or (c) as defined hereinbefore, a conservatively modified variant thereof or an alternative CDR: Sequence ID No: 7/CDR/Sequence ID No: 8/CDR/Sequence ID No: 9/CDR/Sequence ID No: 10, i.e.:

```
Glu-Val-Gln-Leu-Leu-Glu-Ser-Gly-Gly-Gly-Leu-Val-Gln-Pro-Gly-Gly-

Ser-Leu-Arg-Leu-Ser-Cys-Ala-Ala-Ser-Gly-Phe-Thr-Phe-Ser-/CDR/-

Trp-Val-Arg-Gln-Ala-Pro-Gly-Lys-Gly-Leu-Glu-Trp-Val-Ser-/CDR/-

Arg-Phe-Thr-Ile-Ser-Arg-Asp-Asn-Ser-Lys-Asn-Thr-Leu-Tyr-Leu-Gln-

Met-Asn-Ser-Leu-Arg-Ala-Glu-Asp-Thr-Ala-Val-Tyr-Tyr-Cys-Ala-Lys-

/CDR/-Trp-Gly-Gln-Gly-Thr-Leu-Val-Thr-Val-Ser-Ser.
```

In a preferred antibody containing all three CDRs, the heavy chain variable region comprises the following sequence:

```
Glu-Val-Gln-Leu-Leu-Glu-Ser-Gly-Gly-Gly-Leu-Val-Gln-Pro-Gly-Gly-     (Sequence ID No:11)

Ser-Leu-Arg-Leu-Ser-Cys-Ala-Ala-Ser-Gly-Phe-Thr-Phe-Ser-Ser-Phe-

Pro-Met-Ala-Trp-Val-Arg-Gln-Ala-Pro-Gly-Lys-Gly-Leu-Glu-Trp-Val-

Ser-Thr-Ile-Ser-Thr-Ser-Gly-Gly-Arg-Thr-Tyr-Tyr-Arg-Asp-Ser-Val-

Lys-Gly-Arg-Phe-Thr-Ile-Ser-Arg-Asp-Asn-Ser-Lys-Asn-Thr-Leu-Tyr-

Leu-Gln-Met-Asn-Ser-Leu-Arg-Ala-Glu-Asp-Thr-Ala-Val-Tyr-Tyr-Cys-

Ala-Lys-Phe-Arg-Gln-Tyr-Ser-Gly-Gly-Phe-Asp-Tyr-Trp-Gly-Gln-Gly-

Thr-Leu-Val-Thr-Val-Ser-Ser.
```

Similarly, the one or more CDRs of the light chain of the rat CD3 antibody are therefore preferably present in a human variable domain framework which has the following amino acid sequence reading in the leader→constant region direction, CDR indicating a CDR (d), (e) and (f) as defined hereinbefore, a conservatively modified variant thereof or an alternative CDR: Sequence ID No: 12/CDR/Sequence ID No: 13/CDR/Sequence ID No: 14/CDR/Sequence ID No: 15, i.e.:

```
Asp-Phe-Met-Leu-Thr-Gln-Pro-His-Ser-Val-Ser-Glu-Ser-Pro-Gly-Lys-

Thr-Val-Ile-Ile-Ser-Cys-/CDR/-Trp-Tyr-Gln-Gln-Arg-Pro-Gly-Arg-Ala-

Pro-Thr-Thr-Val-Ile-Phe-/CDR/-Gly-Val-Pro-Asp-Arg-Phe-Ser-Gly-Ser-

Ile-Asp-Arg-Ser-Ser-Asn-Ser-Ala-Ser-Leu-Thr-Ile-Ser-Gly-Leu-Gln-

Thr-Glu-Asp-Glu-Ala-Asp-Tyr-Tyr-Cys-/CDR/-Phe-Gly-Gly-Gly-Thr-Lys-

Leu-Thr-Val-Leu.
```

In a preferred antibody containing all three CDRs the light chain variable region comprises the following sequence:

```
Asp-Phe-Met-Leu-Thr-Gln-Pro-His-Ser-Val-Ser-Glu-Ser-Pro-Gly-Lys-    (Sequence ID No:16)

Thr-Val-Ile-Ile-Ser-Cys-Thr-Leu-Ser-Ser-Gly-Asn-Ile-Glu-Asn-Asn-

Tyr-Val-His-Trp-Tyr-Gln-Gln-Arg-Pro-Gly-Arg-Ala-Pro-Thr-Thr-Val-

Ile-Phe-Asp-Asp-Asp-Lys-Arg-Pro-Asp-Gly-Val-Pro-Asp-Arg-Phe-Ser-

Gly-Ser-Ile-Asp-Arg-Ser-Ser-Asn-Ser-Ala-Ser-Leu-Thr-Ile-Ser-Gly-

Leu-Gln-Thr-Glu-Asp-Glu-Ala-Asp-Tyr-Tyr-Cys-His-Ser-Tyr-Val-Ser-

Ser-Phe-Asn-Val-Phe-Gly-Gly-Gly-Thr-Lys-Leu-Thr-Val-Leu.
```

The variable domains comprising one or more CDRs as described above, preferably in the humanised form having human antibody-derived framework regions, may conveniently be attached to another protein or carrier, or to constant domains of light and heavy chains of antibodies.

The nature of the heavy and light chain constant regions has less effect on binding affinity than that of the variable domain framework and these can be based on antibodies of different types as desired, but are preferably of or are derived from those of human origin and may be of various different classes although for the light chain the constant region will most usually be of the lambda type and for the heavy chain it may conveniently be of an IgG class, particularly IgG1. Thus the constant domains may conveniently be selected to have desired effector functions appropriate to the intended therapeutic use of the antibody.

It will also be appreciated that an antibody according to the invention may be used in a form which retains the CDRs but lacks other parts of the molecule not essential to its binding function. In particular as indicated hereinbefore, Fab' and F(ab')$_2$ fragments may be used, or the variable regions incorporating the CDRs of the invention may be attached to a suitable protein or carrier molecule.

It is well recognised in the art that the replacement of one amino acid with another amino acid having similar properties, for example the replacement of a glutamic acid residue with an aspartic acid residue, may not substantially alter the properties or structure of the peptide or protein in which the substitution or substitutions were made. Thus, the invention includes those CDR amino acid sequences in which such a substitution or substitutions have occurred without substantially altering the binding affinity and specificity of the CDRs. Alternatively, deletions may be made in the amino acid residue sequence of the CDRs or the sequences may be extended at one or both of the N- and C-termini whilst still retaining activity.

As indicated, therefore, the invention extends to ligands in which the CDRs may be conservatively modified to provide a variant thereof which retains a binding affinity for the CD3 antigen. Preferred ligands are such that the affinity constant for the antigen is $10^5$ mole$^{-1}$ or more, for example up to $10^{12}$ mole$^{-1}$. Ligands of different affinities may be suitable for different uses so that, for example, an affinity of $10^6$, $10^7$ or $10^8$ mole$^{-1}$ or more may be appropriate in some cases. However ligands with an affinity in the range of $10^6$ to $10^8$ mole$^{-1}$ will often be suitable. Conveniently the ligands also do not exhibit any substantial binding affinity for other antigens. Binding affinities of the ligand and ligand specificity may be tested by assay procedures such as those described in the Examples section hereinafter, (Effector Cell Retargetting Assay), or by techniques such as ELISA and other immunoassays.

The ligands of the invention may be prepared in a number of ways. Most conveniently, however, appropriate gene constructs for the constant and variable regions of the heavy and light chains which are present in the ligand are separately obtained and then inserted in a suitable expression system. Antibody fragment may be prepared from whole antibody molecules in the usual manner or, as described for monovalent antibody fragments hereinbefore, may be produced directly by the expression system.

Genes encoding the variable domains of a ligand of the desired structure may be produced and conveniently attached to genes encoding the constant domains of an antibody of the desired isotype and therapeutic applicability. These constant genes may be obtained from hybridoma cDNA or from the chromosomal DNA or by mutagenesis (site directed) of such genes to produce constant regions with novel properties. Genes encoding the variable regions may also be derived by gene synthesis techniques used in the identification of the CDRs contained herein. Suitable cloning vehicles for the DNA may be of various types.

Expression of these genes through culture of a cell system to produce a functional CD3 ligand is most conveniently effected by transforming a suitable prokaryotic or particularly eukaryotic cell system, particularly an immortalised mammalian cell line such as a myeloma cell line, for example the YB2/3.01/Ag20 (hereinafter referred to as YO) rat myeloma cell, or Chinese hamster ovary cells (although the use of plant cells is also of interest), with expression vectors which include DNA coding for the various antibody regions, and then culturing the transformed cell system to produce the desired antibody. Such general techniques of use for the manufacture of ligands according to the present invention are well known in the very considerable art of genetic engineering and are described in publications such as "Molecular Cloning" by Sambrook, Fritsch and Maniatis, Cold Spring Harbour Laboratory Press, 1989 (2nd edition). The techniques are further illustrated by the Examples contained herein.

Accordingly, the invention further comprises DNA sequences encoding the CDRs of the ligand/antibody of the invention. A group of nucleotide sequences coding for the CDRs (a) to (f) described hereinbefore is as indicated under (a) to (f) below, respectively, but it will be appreciated that the degeneracy of the genetic code permits variations to be made in these sequences whilst still encoding for the CDRs' amino acid sequences.

(a) AGCTTCCAA TGGCC (Sequence ID No: 16)
(b) ACCATTAGTA CTAGTGGTGG TAGAACTTAC TATCGAGACT CCGTGAAGGG C (Sequence ID No: 17)
(c) TTTCGGCAGT ACAGTGGTGG CTTTGATTAC (Sequence ID No: 18)
(d) ACACTCAGCT CTGGTAACAT AGAAAACAAC TATGTGCAC (Sequence ID No: 19)
(e) GATGATGATA AGAGACCGGA T (Sequence ID No: 20)
(f) CATTCTTATG TTAGTAGTTT TAATGTT (Sequence ID No: 21)

The invention also particularly includes larger DNA sequences which comprise (1) DNA expressing human heavy chain framework regions and one or more of (a), (b) and (c), and (2) DNA expressing human light chain framework regions and one or more of (d), (e) and (f). A specific example of such DNA is that sequence (1) indicated below which codes for the CDRs (a), (b) and (c) arranged in the heavy chain framework coded for by the human VH type III gene VH26.D.J. as discussed hereinbefore and that sequence (2) indicated below which codes for the CDRs (d), (e) and (f) arranged in the light chain framework coded for by the human $V_L\lambda$ type VI gene SUT. The CDR sequences (a), (b), (c), (d), (e) and (f) have been underlined.

The humanised ligands in accordance with the invention have therapeutic value. In particular, a reshaped antibody, especially a humanised antibody, with a specificity for the antigen CD3 has valuable applications in immunosuppression, particularly in the control of graft rejection, and potentially also in other areas such as the treatment of cancer, especially of lymphoid malignancies and indeed lymphomas in general.

In a further aspect, the invention thus includes a method of treating patients with lymphomas or for immunosuppression purposes, for instance in a case where graft rejection may occur, comprising administering a therapeutically effective amount of a ligand in accordance with the invention.

Ligands in accordance with the invention may be formulated for administration to patients by administering the said ligand together with a physiologically acceptable diluent or carrier. The ligands are preferably administered in an injectable form together with such a diluent or carrier which is sterile and pyrogen free. By way of guidance it may be stated that a suitable dose of ligand is about 1–10 mg injected daily over a time period of, for example 10 days. In order to avoid a severe first dose response, suitable anti-cytokines may be administered with the first injection. Such a procedure facilitates the use of a dosage towards the upper end of the 1–10 mg range or even somewhat higher.

The invention is illustrated by the following Examples which are illustrated by the drawings listed below:

Position and sequence of the oligonucleotide forward and backward primers used in the cDNA synthesis and PCR amplification of the rat YTH12.5 VL lambda gene.

FIG. 2

Cloning and reshaping of the YTH12.5 VH gene.

Figure 3A:
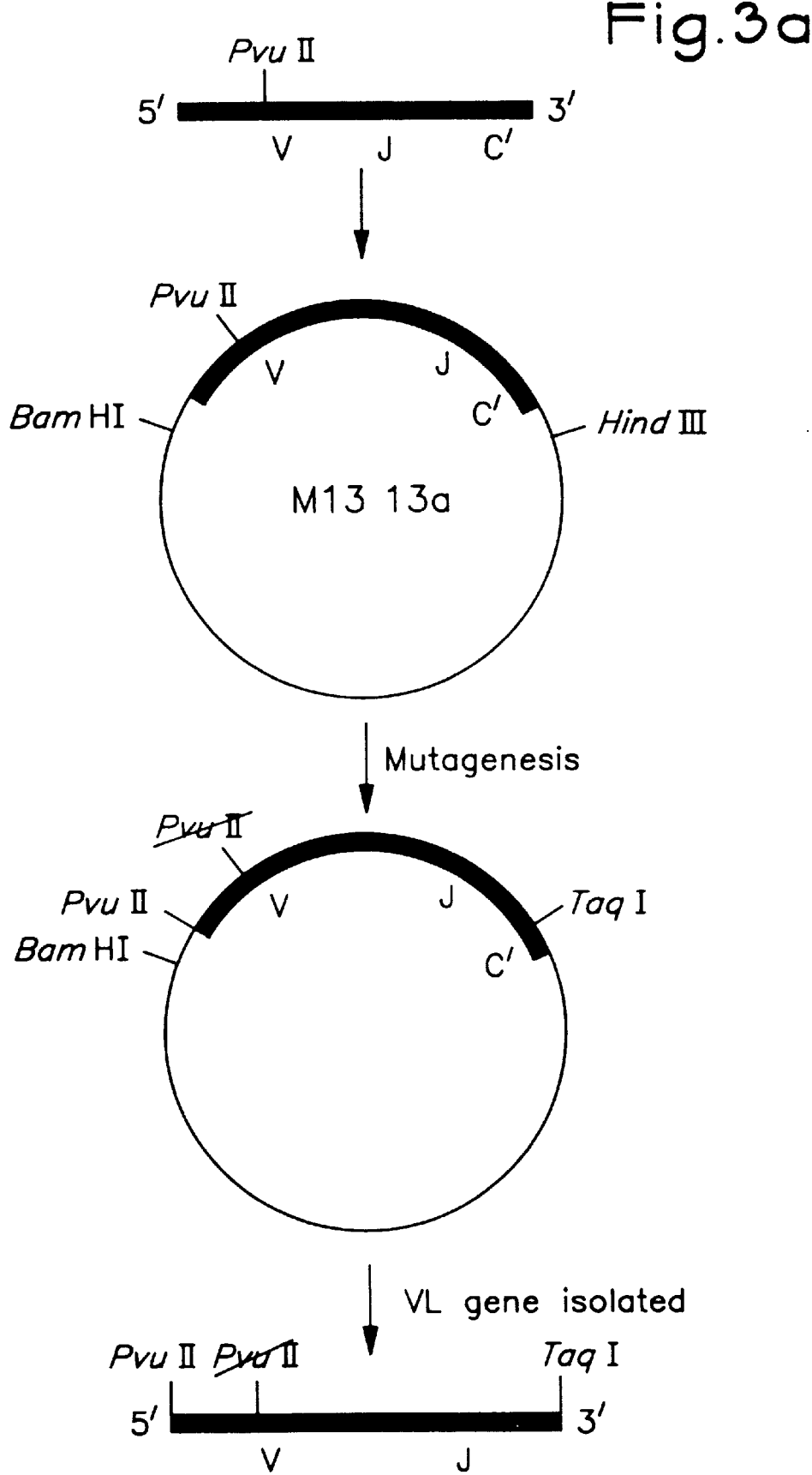
Figure 3B:
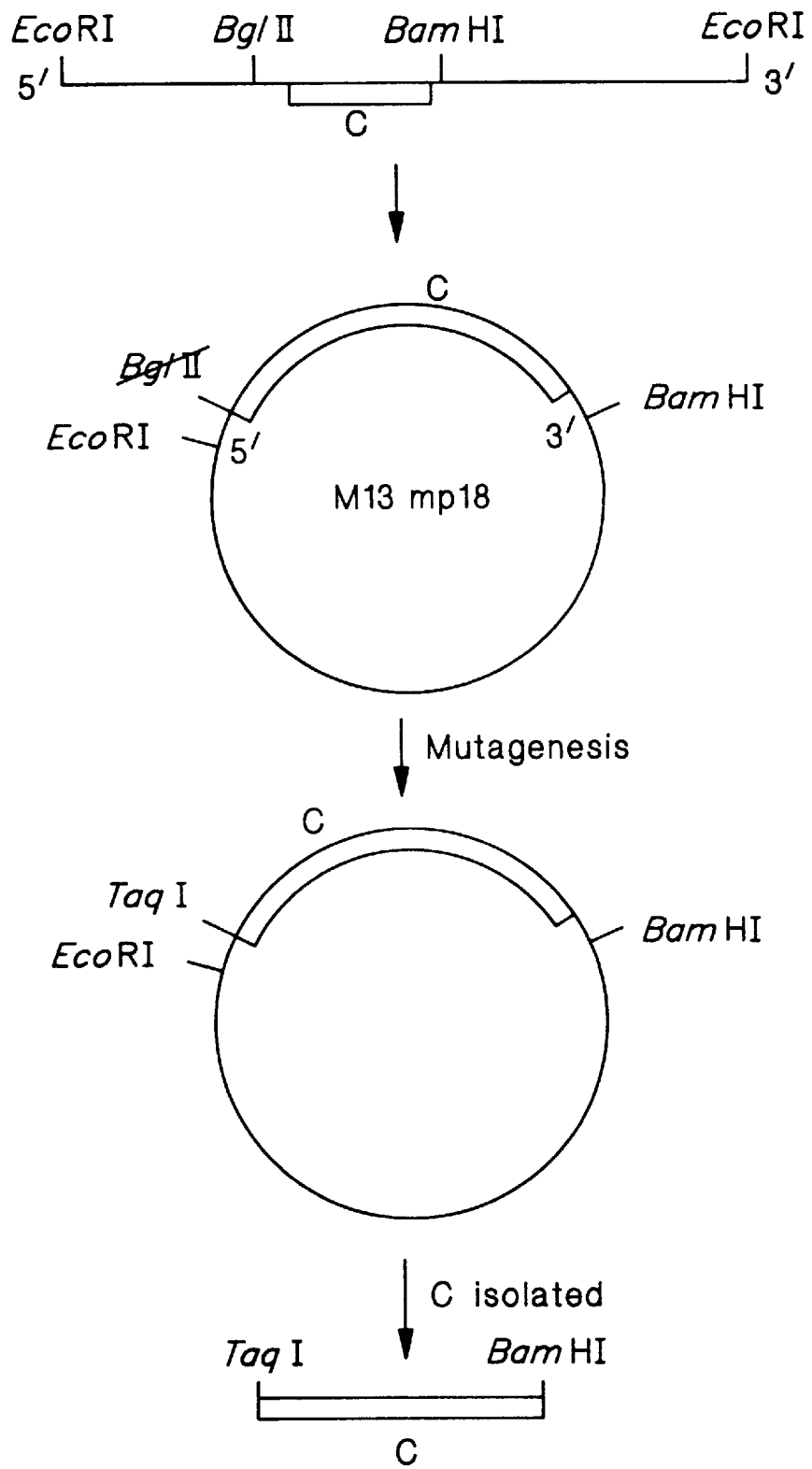
Figure 3C:
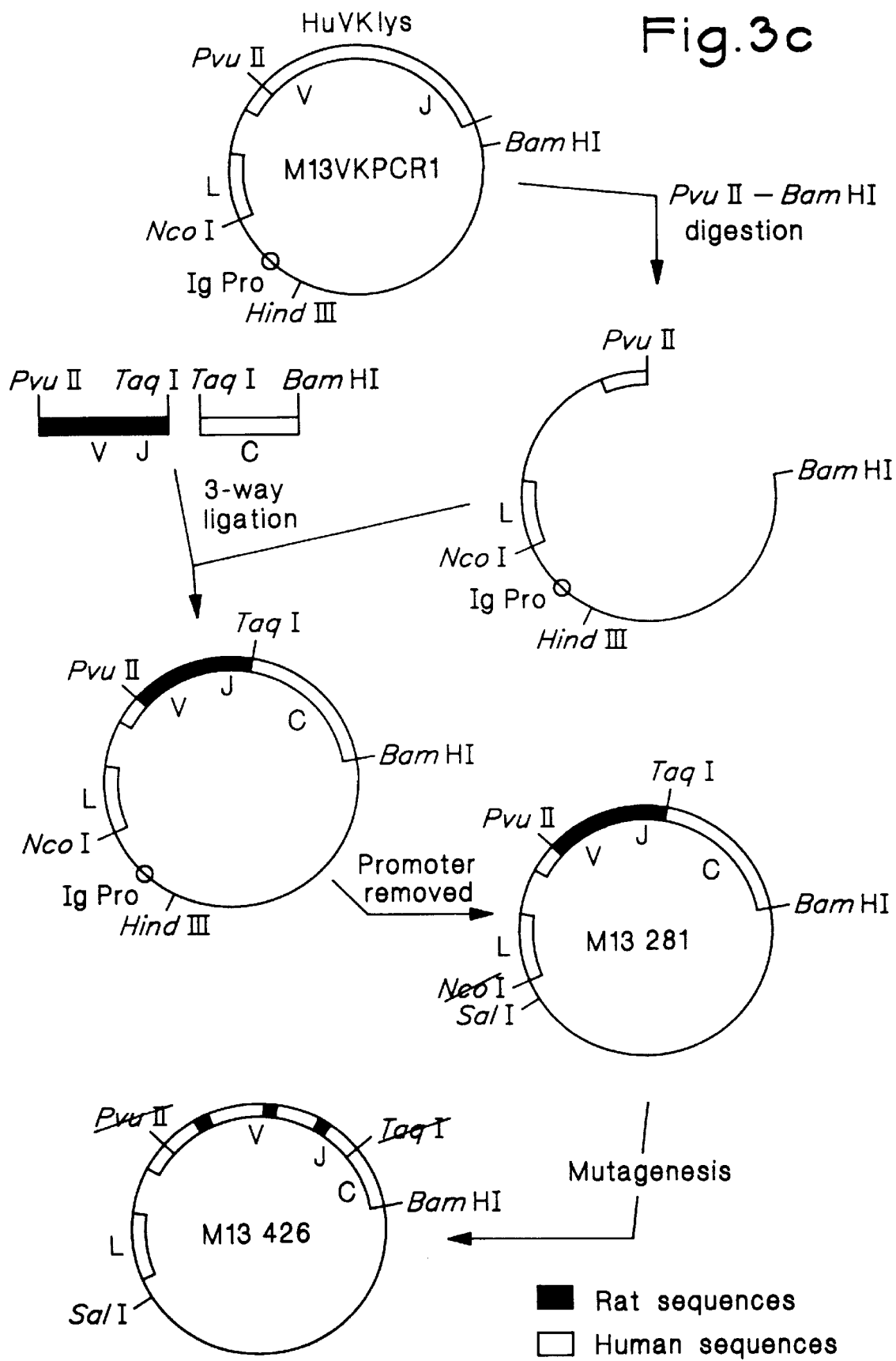

FIGS. 3a–3c

Reshaping of the YTH12.5 VL gene and construction of the YTH12.5 immunoglobulin light chain expression vector.

Figure 4A:
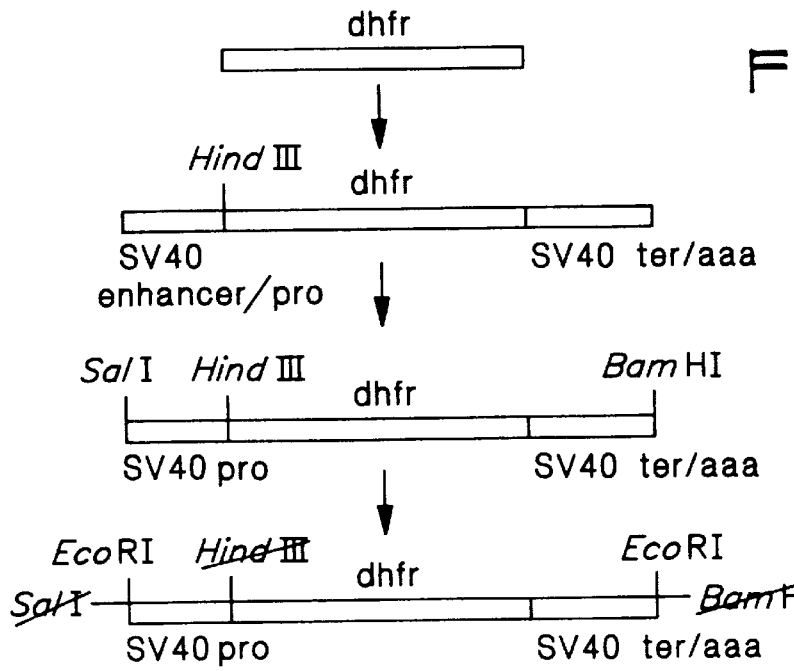
Figure 4B:
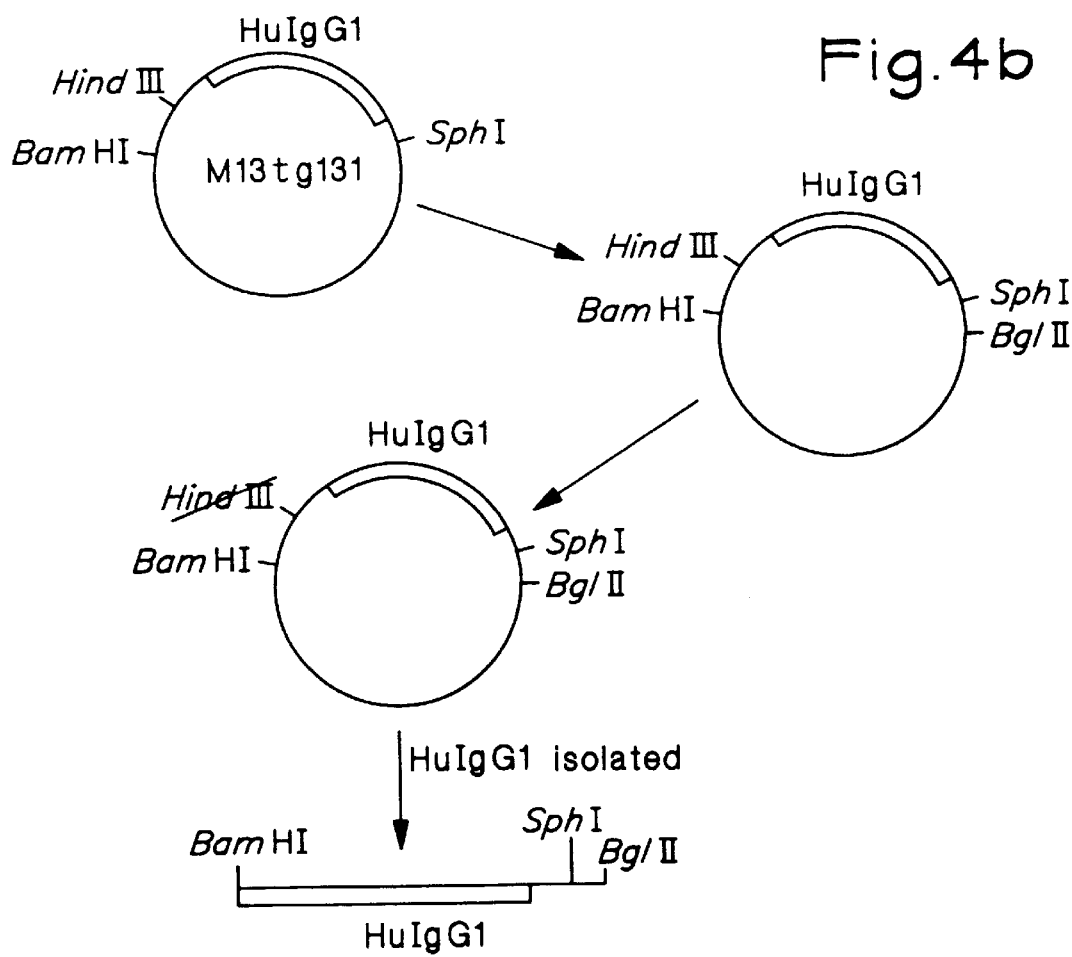
Figure 4C:
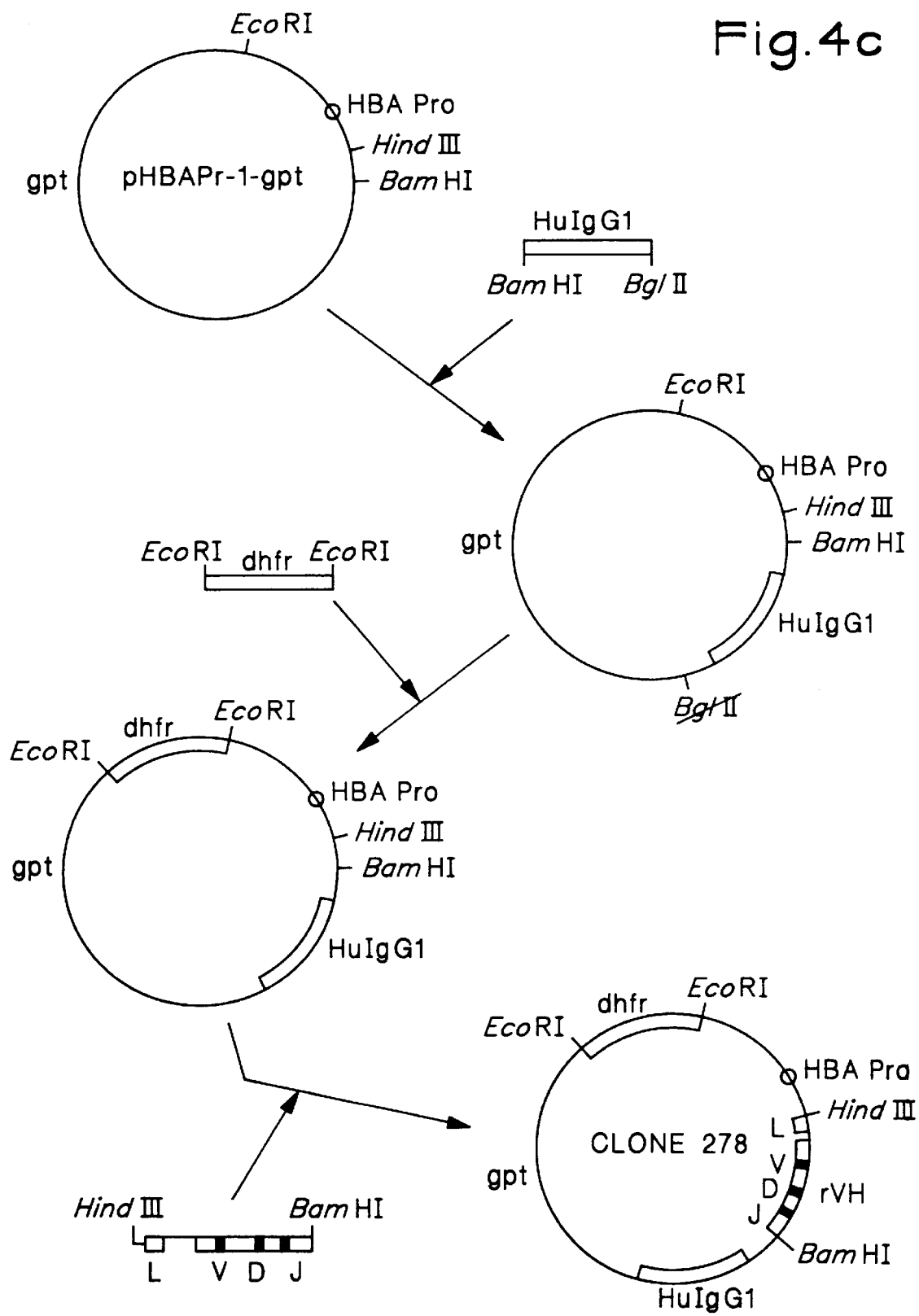

FIGS. 4a–4c

```
(1)  GAGGTCCAAC TGCTGGAGTC TGGGGGCGGT TTAGTGCAGC CTGGAGGGTC      (Sequence ID No:23)

CCTGAGACTC TCCTGTGCAG CCTCAGGATT CACTTTCAGT AGCTTTCCAA

TGGCCTGGGT CCGCCAGGCT CCAGGGAAGG GTCTGGAGTG GGTCTCAACC

ATTAGTACTA GTGGTGGTAG AACTTACTAT CGAGACTCCG TGAAGGGCCG

ATTCACTATC TCCAGAGATA ATAGCAAAAA TACCCTATAC CTGCAAATGA

ATAGTCTGAG GGCTGAGGAC ACGGCCGTCT ATTACTGTGC AAAATTTCGG

CAGTACAGTG GTGGCTTTGA TTACTGGGGC AAGGGACCC  TGGTCACCGT

CTCCTCA (2)  GACTTCATGC TGACTCAGCC CCACTCTGTG TCTGAGTCTC CCGGAAAGAC      (Sequence ID No:24)

AGTCATTATT TCTTGCACAC TCAGCTCTGG TAACATAGAA AACAACTATG

TGCACTGGTA CCAGCAAAGG CCGGGAAGAG CTCCCACCAC TGTGATTTTC

GATGATGATA AGAGACCGGA TGGTGTCCCT GACAGGTTCT CTGGCTCCAT

TGACAGGTCT TCCAACTCAG CCTCCCTGAC AATCAGTGGT CTGCAAACTG

AAGATGAAGC TGACTACTAC TGTCATTCTT ATGTTAGTAG TTTTAATGTT

TTCGGCGGTG GAACAAAGCT CACTGTCCTT
```

Construction of the reshaped YTH12.5 immunoglobulin heavy chain expression vector.

FIG. 5

Construction of the truncated human IgG1 heavy chain (tH) gene expression vector.

FIG. 6

Native PAGE of protein-A purified total immunoglobulin secreted by cells co-transfected with the humanised CD3 heavy, light and truncated heavy chain gene expression vectors.

FIG. 7a–7b

Reduced (7a) and non-reduced (7b) SDS-PAGE of the antibody molecules corresponding to native PAGE bands 1, 2 and 3 (lanes 1, 2 and 3 respectively).

FIG. 8

Humanised bivalent and monovalent CD3 antibodies were tested for their ability to direct T-cell killing of Fc receptor-bearing U937 cells. Rat bivalent YTH12.5 CD3 monoclonal antibody and the humanised CDw52 antibody were tested as controls.

FIG. 9

Comparison of antibody binding of humanised monovalent and bivalent CD3 antibodies with rat bivalent YTH12.5 CD3 monoclonal antibody. The humanised CDw52 antibody was included as a negative control.

FIG. 10

Humanised bivalent and monovalent CD3 monoclonal antibodies were tested for their ability to direct complement mediated lysis of human T-cell blasts. Rat bivalent YTH12.5 CD3 monoclonal antibody was tested for comparison.

EXAMPLES

The invention is illustrated by the following Examples, which employ techniques such as those described in Molecular Cloning by Sambrook et al.

Example 1

Culture of Rat Hybridoma and Chinese Hamster Ovary Cells

YTH12.5 rat hybridoma cells secreting rat gamma-2b antibody specific for the Epsilon chain of the human CD3 antigen complex (Clark et al, Eur. J. Immunol., 19, 381–388 (1989)) were grown or maintained in Iscove's modification of Dulbecco's medium with antibiotics and 5% bovine foetal calf serum respectively. YO cells, a non-antibody secreting rat myeloma cell line were similarly cultured (Clark and Milstein, Somatic Cell Genetics, 7 (6) 657–666, (1981) and European Patent 0043718).

Chinese hamster ovary (CHO) cells with a dihydrofolate reductase negative (dhfr⁻) phenotype were cultured in medium supplemented with hypoxanthine and thymidine.

Example 2

Cloning the YTH12.5 Hybridoma Immunoglobulin Variable Heavy (VH) and Variable Light (VL) Region Genes YTH12.5 cells were lysed with a solution of guanidine thiocyanate and total RNA was isolated by centrifugation through a CsCl cushion (Chirgwin et al, Biochemistry, 18, 5294 (19879)). Messenger RNA was prepared from this by affinity chromatography on oligo-dT cellulose (Maniatis et al, Molecular Cloning. A laboratory manual. Published by Cold Spring Harbour Laboratory. (1982)).

Figure 1:
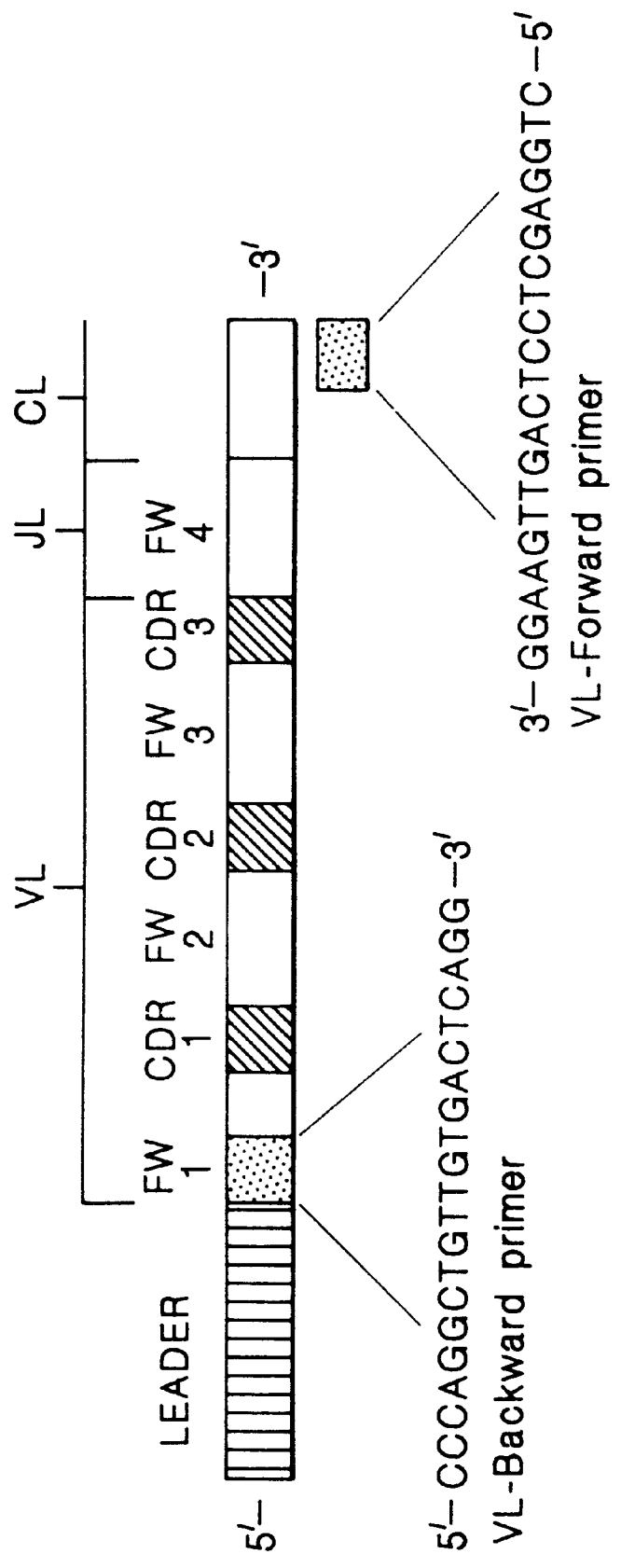
FIG. 1

CDNA synthesis of the YT12.5 VH and VL region genes and their subsequent amplification using the Polymerase Chain Reaction (PCR) was carried out as described by Orlandi et al, Proc. Natl. Acad. Sci., USA, 86, 3833–3837 (1989)). The oligonucleotide primers VH1-forward and VH1-backward, and the specialised M13VHPCR1 cloning vector used during this process for the VH gene were also described by Orlandi et al. CDNA synthesis and amplification of the VL gene was performed using forward and backward oligonucleotide primers derived from a published rat lambda VL gene sequence (Steen et al, Gene, 55, 75–84 (1987)) (FIG. 1). FIG. 1 shows the position and sequence of the oligonucleotide forward and backward primers used in the cDNA synthesis and PCR amplification of the YTH12.5 rat VL lambda gene. In FIG. 1, FW denotes a framework region, VL denotes the light chain variable region, JL the light chain joining region and CL denotes the 5' end of the light chain constant region.

Figure 2:
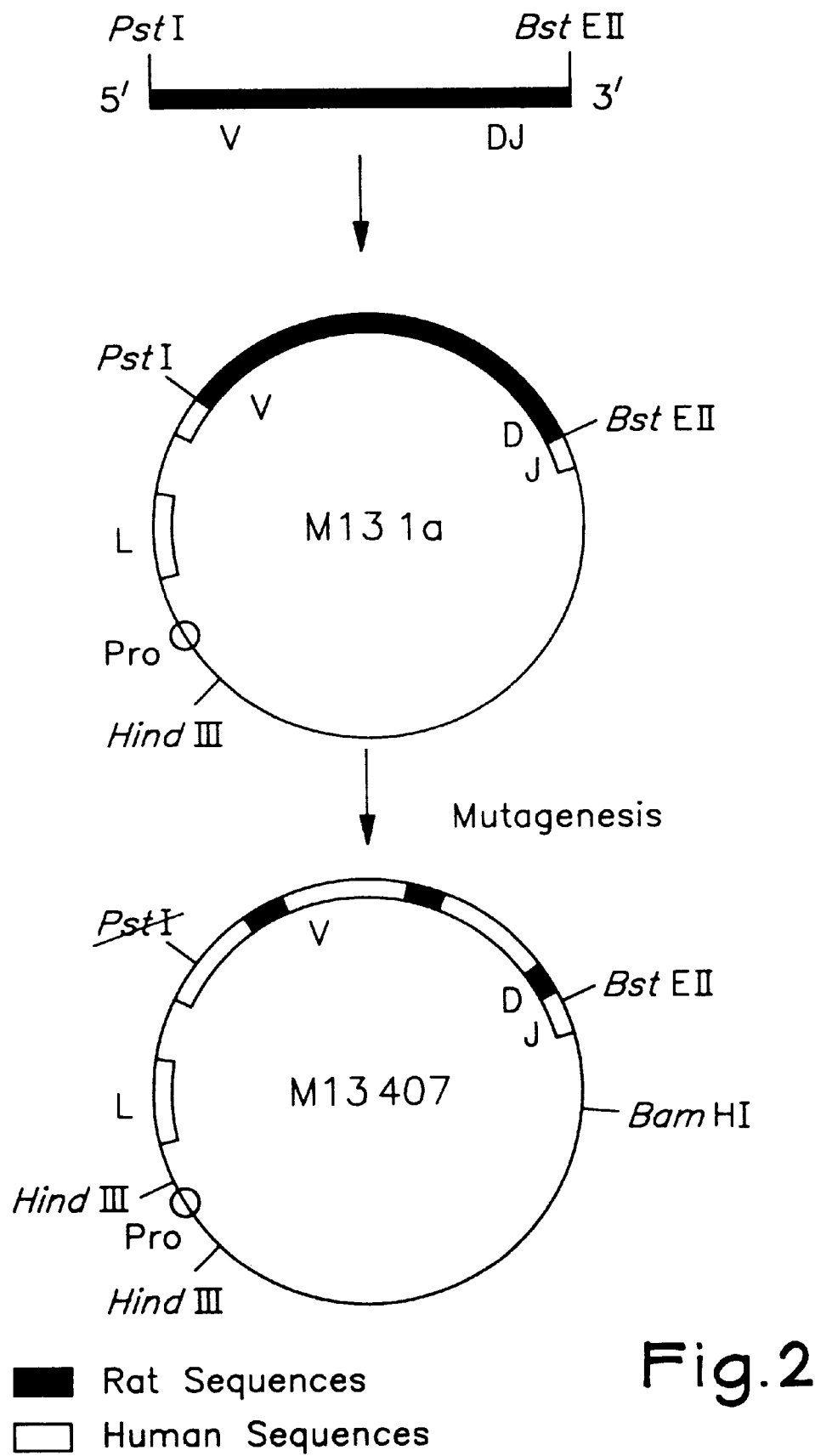

The VL PCR product was cloned by blunt end ligation into HincII cut M13mp18 (FIG. 2). The resulting clone was known as M13 1a. Dideoxy-DNA sequencing was used to identify clones containing VH and VL inserts.

Example 3

Selection of the Variable Domain Framework Regions

A search of the Genbank, EMBL and Swissprot databases identified those known human VH and VL amino acid sequences which had the highest degree of homology to the YTH12.5 VH and VL region genes. When choosing the final human sequence to reshape to, preference was given to the one where the length of the frameworks and complementarity determining regions (CDRs; as defined by Kabat et al, Sequences of proteins of immunological interest; 4th edition. Publ. US Department of Health and Human Services (1987)) were closest to those of the corresponding rat gene. The frameworks chosen for the reshaping of the rat VH and VL genes were from the human VH type III gene VH26-D-J (from the B cell hybridoma cell line 18/2; Genbank code: Humighat. Derismonian et al, J. Immunol., 139, 2496–2501 (1987)) and the human VL lambda type VI gene SUT (Swissprot code: Lv6c$h. Solomon et al, (In) Amyloidosis, pp 449–462. Eds. Glenner, G. G., Osserman, E. F., Benditt, E. P., Calkins, E., Cohen, A. S. and Zucker-Franklin, D. Publ. Plenum Press, New York (1986)), respectively.

Example 4

Reshaping the YTH12.5 VH Gene

The procedure for reshaping the YTH12.5 VH gene is indicated in FIG. 2. In FIG. 2, V, D and J denote the variable, diversity and joining region of the VH gene respectively. The leader sequence is denoted as L, and the immunoglobulin gene promoter as Ig Pro.

Oligonucleotide site directed mutagenesis was performed using the mutagenesis kit supplied by Amersham International PLC. Six mutagenic oligonucleotides ranging in length from 30 to 60 bases were used which were complementary to the positive DNA strand of the VH gene. The M13 clone 1a was used as the template in the mutagenesis reactions to reshape the frameworks (FIG. 2) and mutants were analysed by dideoxy-DNA sequencing. In addition to the mutations necessary for altering the appropriate VH framework codons, a HindIII site was introduced immediately 5' to the VH start codon using a seventh oligonucleotide (FIG. 2c); this was to facilitate removal of the M13VHPCR1 immunoglobulin promotor by HindIII digestion. The M13 clone was known as M13 407. The amino acid sequences coded for by the rat VH gene (bottom sequence: Sequence ID No: 25) and the reshaped VH gene (top sequence: Sequence ID No: 11) are shown below with the CDRs being underlined in the latter (a dash in the rat sequence indicates identity for that residue with the reshaped sequence):

```
Glu-Val-Gln-Leu-Leu-Glu-Ser-Gly-Gly-Gly-Leu-Val-Gln-Pro-Gly-Gly-
  Gln  -   -   -  Gln  -   -   -   -   -   -   -   -   -   -  Arg

Ser-Leu-Arg-Leu-Ser-Cys-Ala-Ala-Ser-Gly-Phe-Thr-Phe-Ser-Ser-Phe-
  -  Met-Lys  -   -   -   -   -   -   -   -   -   -   -   -   -

Pro-Met-Ala-Trp-Val-Arg-Gln-Ala-Pro-Gly-Lys-Gly-Leu-Glu-Trp-Val-
  -   -   -   -   -   -   -   -   -   -  Lys  -   -   -   -   -

Ser-Thr-Ile-Ser-Thr-Ser-Gly-Gly-Arg-Thr-Tyr-Tyr-Arg-Asp-Ser-Val-
Ala  -   -   -   -   -   -   -   -   -   -   -   -   -   -   -

Lys-Gly-Arg-Phe-Thr-Ile-Ser-Arg-Asp-Asn-Ser-Lys-Asn-Thr-Leu-Tyr-
  -   -   -   -   -   -   -   -   -   -  Gly  -  Ser-Ile  -   -

Leu-Gln-Met-Asn-Ser-Leu-Arg-Ala-Glu-Asp-Thr-Ala-Val-Tyr-Tyr-Cys-
  -   -   -   -   -   -   -  Ser  -   -   -  Thr  -   -   -   -

Ala-Lys-Phe-Arg-Gln-Tyr-Ser-Gly-Gly-Phe-Asp-Tyr-Trp-Gly-Gln-Gly-
Ser-Arg  -   -   -   -   -   -   -   -   -   -   -   -   -   -

Thr-Leu-Val-Thr-Val-Ser-Ser
  -  Thr  -   -   -   -   -
```

The sequences shown in the box are coded for by the VH forward and backward PCR primers and may not be the true YTH12.5 VH region sequence.

The nucleotide sequence (Sequence ID No: 23) of the reshaped VH gene is shown below with the CDR sequences underlined:

```
GAGGTCCAAC TGCTGGAGTC TGGGGGCGGT TTAGTGCAGC CTGGAGGGTC

CCTGAGACTC TCCTGTGCAG CCTCAGGATT CACTTTCAGT AGCTTTCCAA

TGGCCTGGGT CCGCCAGGCT CCAGGGAAGG GTCTGGAGTG GGTCTCAACC

ATTAGTACTA GTGGTGGTAG AACTTACTAT CGAGACTCCG TGAAGGGCCG

ATTCACTATC TCCAGAGATA ATAGCAAAAA TACCCTATAC CTGCAAATGA

ATAGTCTGAG GGCTGAGGAC ACGGCCGTCT ATTACTGTGC AAAATTTCGG

CAGTACAGTG GTGGCTTTGA TTACTGGGGC CAAGGGACCC TGGTCACCGT

CTCCTCA
```

Example 5

Reshaping the YTH12.5 VL Gene

The procedure for reshaping the YTH12.5 VL gene is indicated in FIG. 3. FIG. 3(a) shows the strategy for cloning the rat YTH12.5 VL gene. The abbreviations V and J denote the variable and joining regions of the VL gene. C' denotes the 5' end of the rat YTH12.5 lambda constant region. The PCR product was cloned into M13 to give clone M13 13a. Mutagenesis was carried out to introduce and delete restriction enzyme sites. The VL gene was isolated from M13 13a by PvuII-TaqI digestion.

Originally cloned into M13mp18 (Example 2), the YTH12.5 VL gene lacked upstream and downstream signals necessary for gene expression. Therefore, before reshaping, the VL gene was subcloned into the vector M13VKPCR1 (Orlandi et al, Proc. Natl. Acad. Sci., USA, 86, 3833–3837) (1989)) (FIG. 3(c)+(d) along with the Kern- Oz- human lambda constant region gene (CL) (Rabbitts and Forster, Mol. Biol. Med., 1, 11–19 (1983), isolated as shown in FIG. 3(b) from 8 KB genomic fragment. In FIG. 3(b), C denotes the human Kern-Oz constant region. The cloning vector M13VKPCR1 was prepared by excising out the humanised kappa light chain variable region (HuVKlys) which constitutes part of the M13VKPCR1 cloning vector. Before the three way ligation of vector, VL and CL could be carried out, site directed mutagenesis was necessary to introduce and/or delete appropriate restriction enzyme sites. Details of this process are illustrated in FIGS. 3(a), (b) and (c). The resulting chimaeric rat VL-human CL gene was isolated by NcoI-BamHI digestion and subcloned in between the HindIII and BamHI sites of the vector pHBAPr-1-gpt (Gunning et al, Proc. Natl. Acad. Sci., USA, 84, 4831–4835 (1987)), causing the loss of the M13VKPCR3 immunoglobulin promotor, the NcoI and the HindIII sites. The gene was finally subcloned as a SalI-BamHI fragment into M13mp18 to produce clone 281, the template for the subsequent reshaping mutagenesis reactions. Mutagenesis was performed as described for the rat VH gene; mutagenic oligonucleotides were made complementary to the negative DNA strand of the VL gene due to the orientation of the gene in the M13mp18 vector. Five oligonucleotides ranging in length from 27 to 72 nucleotides were used. The amino acid sequences coded for by the rat VL gene (bottom sequence: Sequence ID No: 26) and the reshaped VL gene (top sequence: Sequence ID No: 15) are shown below with the CDRs being underlined in the latter (a dash in the rat sequence indicates identity for that residue with the reshaped sequence):

```
Asp-Phe-Met-Leu-Thr-Gln-Pro-His-Ser-Val-Ser-Glu-Ser-Pro-Gly-Lys-
  Gln-Ala-Val-Val  -    -  Ala- Asn  -    -    -  Thr  -  Leu  -  Ser

Thr-Val-Ile-Ile-Ser-Cys-Thr-Leu-Ser-Ser-Gly-Asn-Ile-Glu-Asn-Asn-
  -    -  Lys-Leu  -    -    -    -    -    -    -    -    -    -

Tyr-Val-His-Trp-Tyr-Gln-Gln-Arg-Pro-Gly-Arg-Ala-Pro-Thr-Thr-Val-
  -    -    -    -    -    -  Leu-Tyr-Glu  -    -  Ser  -    -    - Met

Ile-Phe-Asp-Asp-Asp-Lys-Arg-Pro-Asp-Gly-Val-Pro-Asp-Arg-Phe-Ser-
  - Tyr  -    -    -    -    -    -    -    -    -    -    -    -

Gly-Ser-Ile-Asp-Arg-Ser-Ser-Asn-Ser-Ala-Ser-Leu-Thr-Ile-Ser-Gly-
  -    -    -    -    -    -    -    -    -  Phe  -    -    - His-Asn

Leu-Gln-Thr-Glu-Asp-Glu-Ala-Asp-Tyr-Tyr-Cys-His-Ser-Tyr-Val-Ser-
Val-Ala-Ile  -    -    -    -  Ile  -  Phe  -    -    -    -    -

Ser-Phe-Asn-Val-Phe-Gly-Gly-Gly-Thr-Lys-Leu-Thr-Val-Leu
  -    -    -    -    -    -    -    -    -    -    -    -    -
```

The amino acid sequence shown in the box is coded for by the Vλ back primer and therefore may or may not be present in the original YTH12.5 Vλ sequence.

The nucleotide sequence (Sequence ID No: 24) of the reshaped VL gene is shown below with the CDR sequences underlined:

```
GACTTCATGC TGACTCAGCC CCACTCTGTG TCTGAGTCTC CCGGAAAGAC

AGTCATTATT TCTTGCACAC TCAGCTCTGG TAACATAGAA AACAACTATG

TGCACTGGTA CCAGCAAAGG CCGGGAAGAG CTCCCACCAC TGTGATTTTC

GATGATGATA AGAGACCGGA TGGTGTCCCT GACAGGTTCT CTGGCTCCAT

TGACAGGTCT TCCAACTCAG CCTCCCTGAC AATCAGTGGT CTGCAAACTG

AAGATGAAGC TGACTACTAC TGTCATTCTT ATGTTAGTAG TTTTAATGTT

TTCGGCGGTG GAACAAAGCT CACTGTCCTT
```

Example 6
Expression of the Reshaped YTH12.5 Immunoglobulin Genes in DHFR⁻CHO Cells An expression vector for the reshaped heavy (H) chain immunoglobulin gene was derived from the vector pHBAPr-1-gpt gpt-EcoRI xanthine-guanine phosphoribosyl transferase gene) as illustrated schematically in FIGS. 4(a), (b) and (c). The human IgG1 genomic constant region gene (HuIgG1) on a 2.2 KB BamHI-BqlII fragment of DNA (Takahashi et al, Cell, 29, 671–679 (1982)) was isolated as shown in FIG. 4(b). The human IgG1 genomic constant region was first inserted into the BamHI site of pHBAPr-1-gpt. A 1.65 KB fragment of DNA encoding the mouse dhfr gene (Chang et al, Nature, 275, 617–624 (1978)) flanked by SV40 early promotor and SV40 early termination and polyadenlyation signals (Subramani et al, Mol. Cell. Biol., 1, 854–864 (1981); with a crippled promotor (isolated as shown in FIG. 4(a)) was then cloned into the EcoRI site, followed by the reshaped YTH12.5 VH gene (see Example 4) in between the vector's HindIII and BamHI sites (to give clone 278).

The reshaped light (L) chain immunoglobulin gene on a SalI-BamHI fragment of DNA was inserted in between the SalI and BamHI sites of the expression vector pHBAPr-1 (Gunning et al, Proc. Natl. Acad. Sci., USA, 84, 4831–4835 (1987)) (to give clone 274). This vector has no eukaryotic cell selectable marker.

The H and L chain expression vectors were linearised by digestion with PvuI and then cotransfected into dhfr⁻. CHO cells using the transfection reagent DOTMA (Boehringer). Stable transfectants were selected by their ability to grow in xanthine/hypoxanthine free IMDM containing dialysed foetal bovine calf serum, a property conferred by the H chain expression vector's dhfr gene. Transfectants, cloned in soft agar and cultured in 24-well plates, were screened for antibody production by ELISA.

Example 7
Enzyme Linked Immunosorbent Assay (Elisa)

Test cell culture supernatants were titrated in Falcon Microtest III flat-bottomed plates which had previously been coated overnight with 1/4000 polyclonal goat anti-human IgFc antibody (Sigma) in PBS, pH 7.4 at 4° C. The presence of captured human antibody was detected using 1/4000 biotinylated polyclonal goat anti-human lambda L chain antibody (Amersham) followed by 1/1000 biotinylated, streptavidin complexed horse-radish peroxidase (Amersham) and the substrate OPD. PBS containing 0.02% v/v Tween 20 and 1% w/v BSA was used as the antibody diluent after the capture antibody stage. Incubations for the test antibody, detector antibody, peroxidase and substrate were 1 hr, 1 hr, 1 hr and 30 min respectively at 37° C.; plates were rinsed 4 times for 3 min in between each stage.

Figure 5:
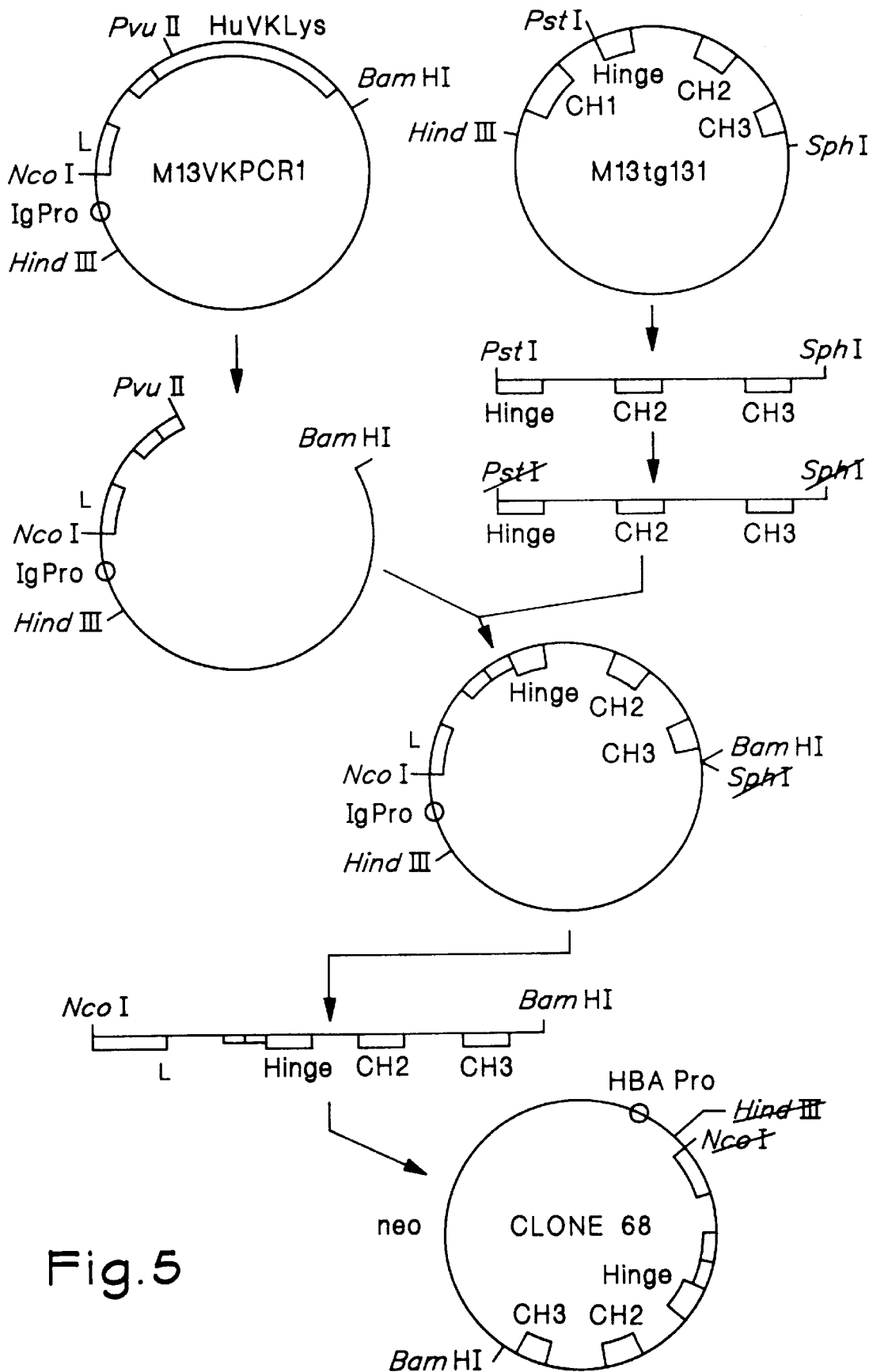

Example 8
Preparation of Monovalent Antibody (1Fab', 1Fc) by the Introduction of an N-Terminal Truncated Human IgG1 Heavy Chain (tH) Gene into an Antibody Secreting Cell Line The human IgG1 genomic constant region gene (Takahashi et al, Cell, 29, 671–679 (1982)) on a 2.2 KB BamHI-SphI fragment of DNA in M13Tg131 was digested with PstI and SphI to yield a 1.4 kB length of DNA encoding the hinge and second and third constant region domain (CH2 and CH3) exons. This fragment was blunt end repaired with T4 DNA polymerase to remove the 3' overhanging single stranded DNA ends produced by the PstI and SphI endonucleases. The truncated gene was then inserted into the vector M13VKPCR1 (Orlandi et al, Proc. Natl. Acad. Sci., USA, 86, 3833–3837 (1989)) between the vector's PvuII and BamHI sites to provide the gene with a start codon and leader peptide sequence necessary for gene expression. The vector's BamHI site was reconstituted by end repair using the Klenow fragment of DNA polymerase 1 during this procedure. The completed gene was excised from M13VKPCR1 by digestion with NcoI and BamHI (thus separating the vector's immunoglobulin promotor from the gene) and then inserted between the HindIII and BamHl sites of the expression vector pHBAPro-I-Neo (Gunning et al, Proc. Natl. Acad. Sci., USA, 85, 7719–7723 (1987)) in which expression is controlled by the human β actin promotor to produce the tH expression vector clone 68. The steps described above are summarised in FIG. 5.

The completed tH gene is predicted to encode a polypeptide comprising a mouse immunoglobulin heavy chain variable region leader peptide followed by the first three N-terminal amino acids of the humanised anti-lysozyme kappa light chain variable region fused to the hinge-CH2-CH3 domains of human IgGl.

Figure 6:
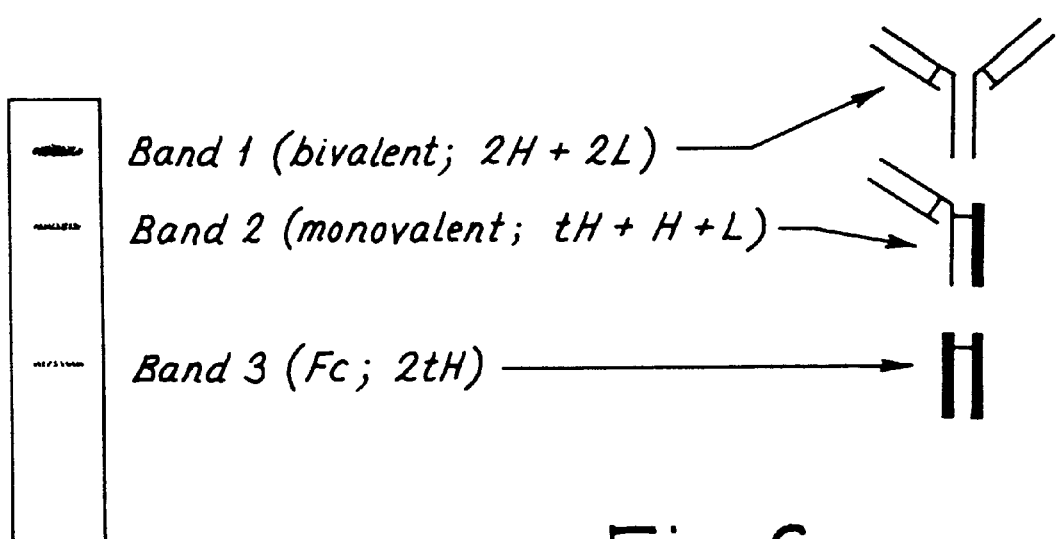
Figures 7A, 7B:
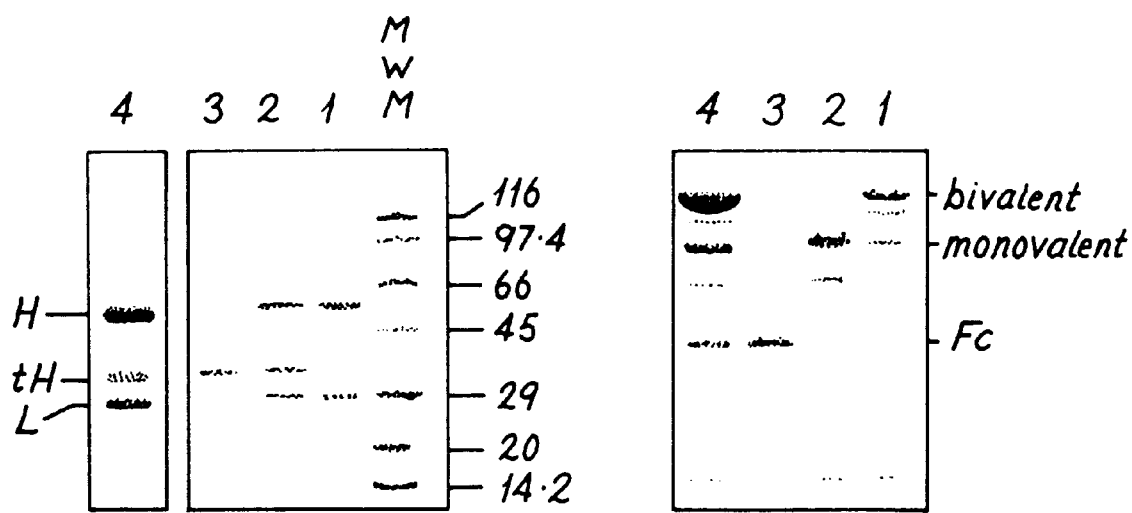

The tH gene expression vector (clone 68) was linearized with PvuI and then transfected into YO or CHO cells along with expression vectors carrying the humanised heavy (vector 276 for YO cells, vector 278 for CHO cells) and light (vector 274) chain genes (see example 6 for details of vectors 274 and 278; vector 276 is identical to 278 with the exception that the EcoRI fragment of DNA carrying the DHFR gene is missing). Transfected YO cells were selected in IMDM containing 5% normal bovine FCS, 2 mg/ml G418, 2 μg/ml mycophenolic acid, 250 μg/ml xanthine, 13.6 μg/ml hypoxanthine and 3.87 μg/ml thymidine. Transfected CHO cells were selected in IMDM containing 5% dialysed bovine FCS and 2 mg/ml G418. Transfectants were screened for the secretion of all three immunoglobulin chains by analysis of total immunoglobulin (prepared by protein-A affinity adsorption) on 10–15% gradient native and SDS polyacrylamide gels using a Pharmacia Phast Gel system.
Results Native (non-denaturing) PAGE analysis of total immunoglobulin (for example, from the cell line EGRY068/H+ L.3.7) revealed the presence of three major protein bands (FIG. 6). Purification of the high molecular weight band (band 1) followed by further PAGE analysis in reducing denaturing conditions showed that it consisted of heavy (H) and light (L) immunoglobulin chains (FIG. 7a). Similarly the protein band of intermediate size (band 2) consisted of H+L+tH polypeptides, and the lower band (band 3) contained only tH polypeptides. The bands can therefore be identified as bivalent antibody. monovalent antibody and Fc molecules respectively. Image analysis of the SDS-PAGE gel using the Pharmacia Phast-Image system indicated that the H, L and tH polypeptides in native PAGE bands 1 and 2 were present within each band in approximately equimolar amounts as expected. Denaturing, non-reducing SDS-PAGE demonstrated that the polypeptides comprising all three native gel protein bands were linked by disulphide bonds. The possibility that the bands represented non-specific aggregates of the H, L and tH polypeptides was therefore ruled out (FIG. 7b).

Example 9

Purification of Antibodies

The monovalent and bivalent humanised CD3 antibodies were purified as follows: Total immunoglobulin was isolated by protein-A affinity chromatography as described by Harlow and Lane (Antibodies: A Laboratory Manual, Publ. Cold Spring Harbor 1988), from the culture supernatant of CHO cells co-transfected with expression vectors carrying the tH, humanised H and L chain genes. The mono- and bivalent antibody species were separated from this mixture by ion-exchange chromatography using an LKB HPLC system fitted with a TSK-5PW-DEAE 7.5×60 mm Glaspac column, equilibrated with 20 mM Tris pH 8.5 and eluted with a gradient of the same buffer containing 1M NaCl. The rat YTH12.5 Mab was similarly purified with the exception that ion exchange chromatography was performed in 20 mM piperazine pH 9.5 containing 0.1% betaine. The humanised CDw52 Mab (IgGl) (Reichmann et al., Nature, 332, 323–327, 1988) produced in CHO cells was provided, protein-A purified, by Dr. G. Hale (Cambridge University Division of Immunology). Antibody concentrations were determined using the Lowry assay, and the purity of antibody preparations was assessed by SDS-PAGE on 10–15% gradient gels using a Pharmacia Phast Gel System.

Example 10

Competitive Binding Assay

Figure 8:
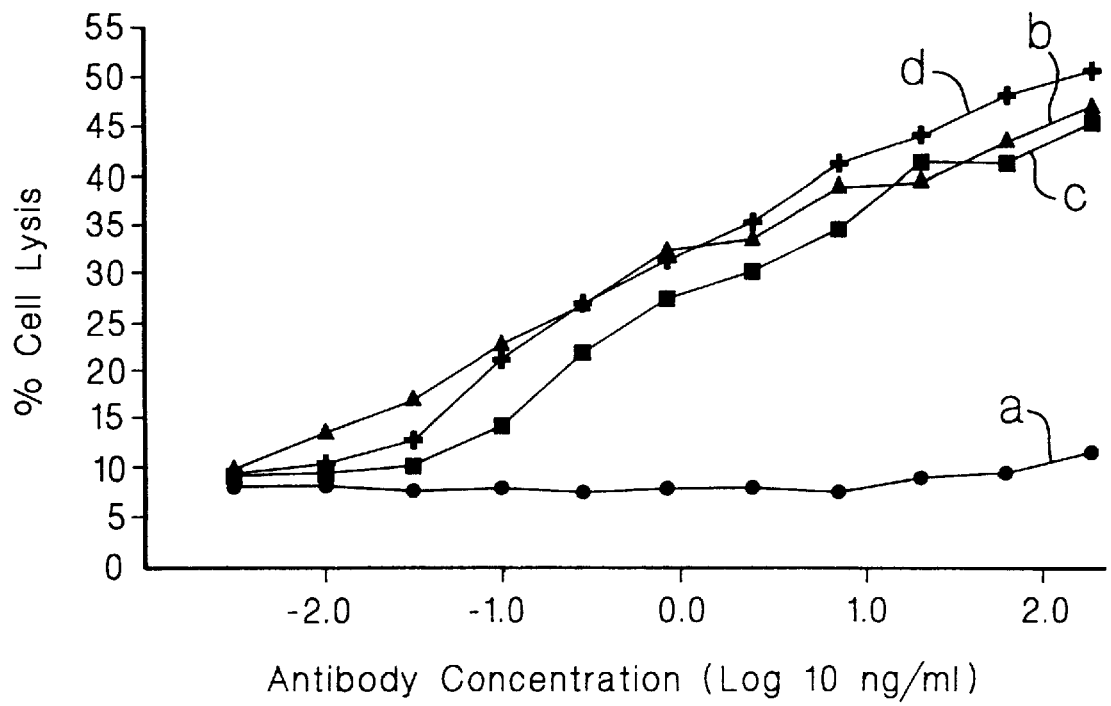

Aliquots of $5 \times 10^4$ HPBALL (human peripheral blood acute lymphoblastic leukaemia) cells in 96 well microtitre plates were stained with 2.0 μg ml$^{-1}$ biotinylated monovalent humanised CD3 monoclonal antibody (prepared from the cell line EGRCHOH+L/68.2) in the presence of increasing concentrations of non-biotinylated competitor Mab. After 1 hour the cells were rinsed and stained for a further 1 hour with streptavidin-FITC (Amersham RPN 1232). The cells were rinsed again and fixed with 1% v/v formaldehyde in PBS. Incubations were performed at 4° C. and PBS containing 0.1% (w/v) sodium azide, 1% w/v BSA and 5% v/v heat inactivated normal rabbit serum was used as the diluent and rinsing solution. The mean cellular fluorescence of approximately 3500 cells per well was determined using a FACScan (Becton Dickinson).
Comparison of antibody binding The results are shown in FIG. 8 wherein (a) is the CDw52 Mab control, (b) is the humanised monovalent CD3 Mab, (c) is the rat YTH12.5 CD3 Mab and (d) is the humanised bivalent CD3 Mab.

1–2 μg ml$^{-1}$ of humanised bivalent CD3 Mab was sufficient to saturate the CD3 antigen binding sites on $5 \times 10^4$ HPBALL cells, whereas 250 μg ml$^{-1}$ of the humanised monovalent CD3 Mab was not enough (data not shown). For this reason the monovalent Mab was used as the biotinylated detector in the competitive binding assays, as relatively low concentrations of the bivalent YTH12.5 rat and humanised CD3 antibodies would be required to achieve a significant degree of competition.

The concentration of the rat and humanised bivalent Mabs required to give 50% competition of the monovalent detector were very similar. Only 1.3-fold more humanised compared to rat Mab was needed.

A 6-fold to 8.25 fold higher concentration (in separate experiments) of the humanised monovalent Mab was necessary to obtain the same degree of competition as the humanised bivalent Mab. As antibody concentration has been expressed in terms of molar Fab' domain concentration (to account for the presence of 2 and 1 antigen binding sites per bivalent and monovalent molecule respectively), this difference must be indicative of the increase in antibody avidity resulting from the linking of two Fab domains in a bivalent Mab molecule. CD3-antigenic modulation by the bivalent Mab can be discounted as the cause because staining was performed in the presence of 15 mM sodium azide at 4° C. Azide at a concentration of 10 mM has been shown to inhibit antibody-induced redistribution of cell surface molecules (Taylor and Duffus, 1971). Nature, New Biol. 233, p. 225.

Example 11

Figure 9:
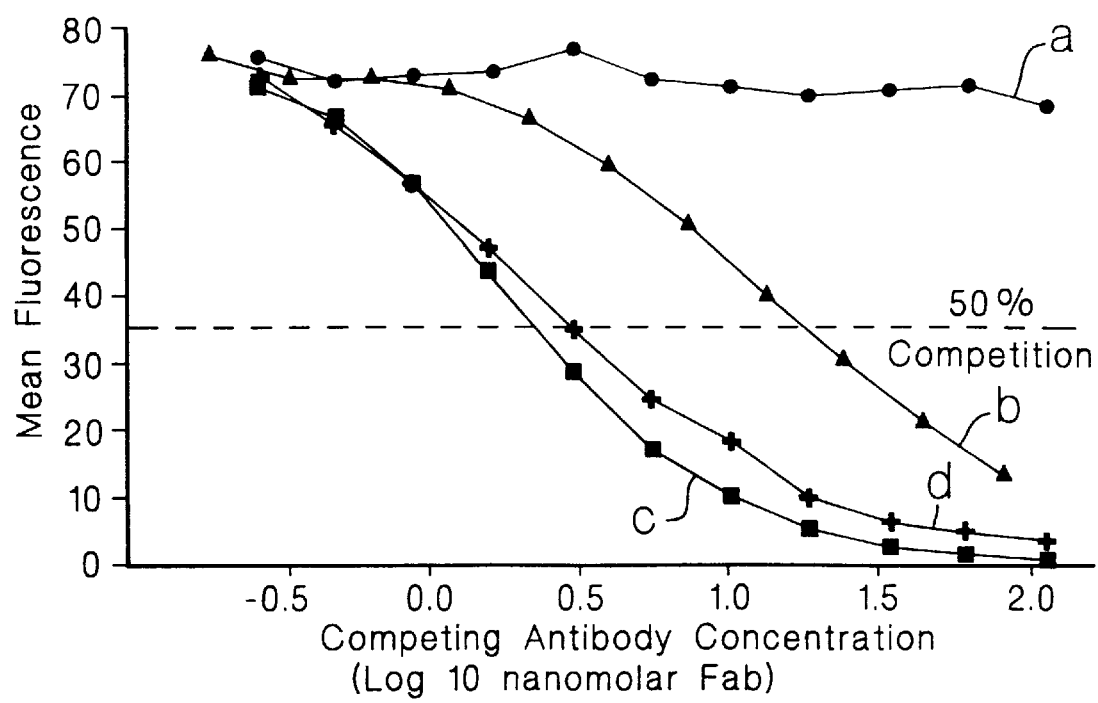

Effector Cell Retargetting Assay for the Detection of Antibody with Human CD3 Antigen Specificity This was performed as described elsewhere (Gilliland et al, Proc. Natl. Acad. Sci., USA, 85, 7719–7723 (1988)). Briefly, $^{51}$Cr labelled U937 human monocytic tumour cells, which express the Fc$\gamma$ receptor 1 molecule, were used as targets. CD3 antigen positive Fc$\gamma$ receptor 1 effector cells were generated from human peripheral blood lymphocytes (PBLs) activated with mitogenic CD3 antibody and maintained in medium containing IL-2. Target and effector cells were mixed at a ratio of 1:2 in the presence of test or control antibody. Lysis of the target cells (indicating cross-linking of targets and cytotoxic effectors by CD3 antigen-CD3 antibody and CD3 antibody (Fc)-Fc$\gamma$ receptor 1 interactions, and hence the presence of CD3 antigen specific antibody) was measured by the quantity of $^{51}$Cr released by the targets into the culture medium. Each antibody dilution was tested in quadruplicate. Humanised CD3 monovalent and bivalent antibodies produced by CHO cell lines were compared with rat YTH12.5 CD3 antibody, humanised anti-CD1 antibody (CDw52) was included as a negative control. The results are shown in FIG. 9 wherein (d) is humanised bivalent CD3 Mab, (c) is rat bivalent YTH12.5 CD3 Mab, (b) is humanised monovalent CD3 Mab and (a) is the CDw52 control. As expected, $^{51}$Cr release from the humanised CDw52 was very low and not affected by increasing or decreasing the amounts of antibody (no dose-response). The humanised CD3 antibodies performed marginally better than the rat YTH12.5 antibody.

Example 12

Complement Mediated Cell Lysis (CML)

The CML activity of the humanised CD3 monoclonal antibodies was compared using 1-cell blasts as targets (see Example 11 for details of their preparation) and serum from the T-cell donor as the source of complement. The assay was essentially carried out as described by Bindon et al., European Journal of Immunology, 18, 1507–1514 (1988). Briefly, aliquots of $1 \times 10^5$ $^{51}$Cr labelled T-cell blasts in 96 well microtitre plates were incubated for 1 hour at 37° C. in the presence of test antibody (at various concentrations) and a final concentration of human serum of 25% v/v. After the incubation, the cells were pelleted by centrifugation. Half of the supernatant was carefully removed from each well and analysed to determine its $^{51}$Cr content.

Figure 10:
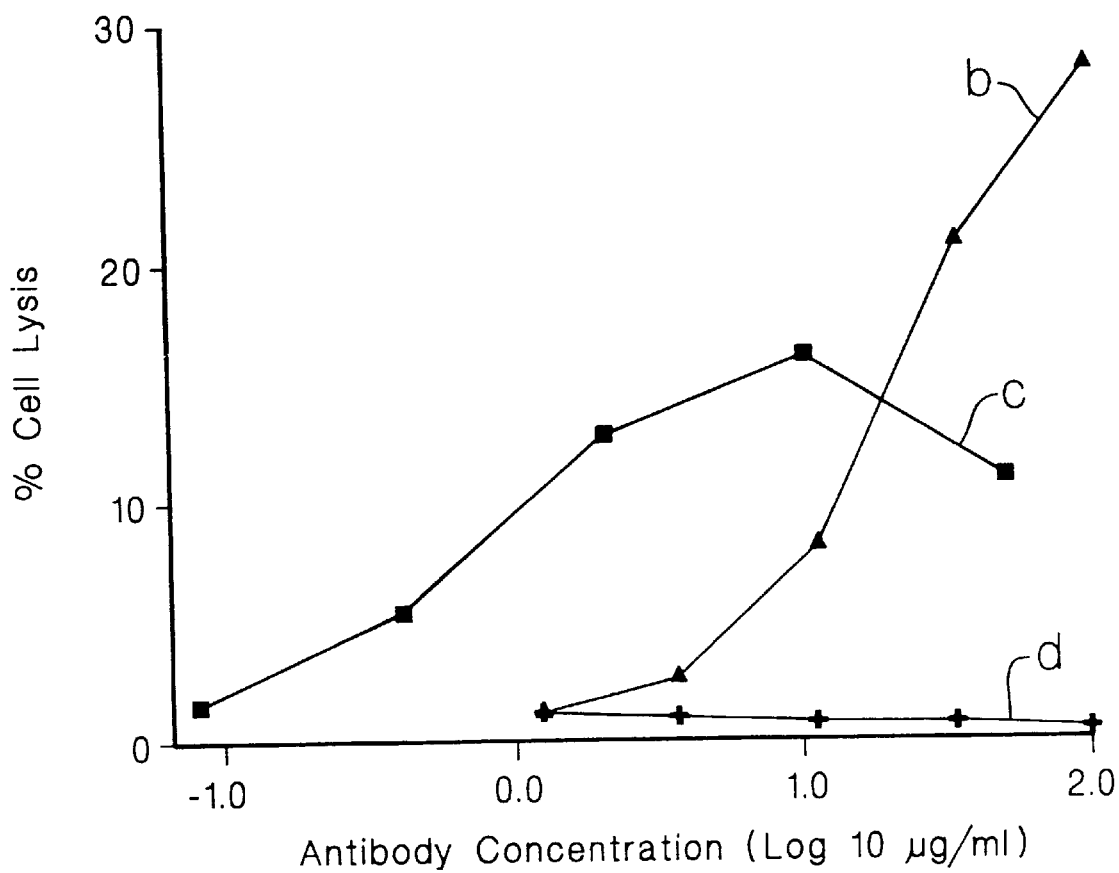

The results are shown in FIG. 10 wherein (d) is humanised bivalent CD3 Mab, (b) is humanised monovalent CD3 Mab and (c) is rat bivalent Mab. Each point represents the mean of two determinations.

The bivalent humanised CD3 Mab gave no detectable lysis at all even at a concentration of 100 $\mu$g ml$^{-1}$, which exceeds the saturation concentration by a factor of approximately 50. Conversely, the difference between the non-lytic bivalent humanised CD3 Mab and its lytic rat Mab counterpart must be due to the different antibody constant regions as the antigen specificities they possess are the same. It is not a result of expressing the humanised antibody in CHO cells, as antibody produced by YO rat myeloma cells behaved in a similar fashion (data not shown).

The effect on CML activity of making the humanised CD3 Mab monovalent was quite dramatic. Whereas the bivalent Mab gave no lysis at 100 $\mu$g ml$^{-1}$, the monovalent Mab gave almost 30% lysis. This is approximately 2-fold higher than the maximum lysis obtained with the bivalent rat YTH12.5 Mab, but it required an antibody concentration 10-fold higher than that of the rat Mab to achieve it. The need for a higher antibody concentration for monovalent Mab CML may be partly due to the difference in binding avidity previously demonstrated for monovalent and bivalent Mabs; thus a higher concentration of monovalent Mab is needed to bind the same amount of antibody to the cell surface.

Using a Mab which effectively lysis cells with complement is presumably an advantage in situations where cell clearance is the aim, but it may not be of over-riding importance. The performance of the humanised CD3 Mabs in the effector-cell retargetting assay which is dependent on Fc-Fc receptor interactions is therefore encouraging.

Note

In this specification the amino-acid residues are designated in the standard manner (Pure and Applied Chemistry, 1974, 40, 317 and European Journal of Biochemistry, 1984, 138, 9) as are the nucleotide residues (Molecular Cloning, Sambrook et al, ibid).

---

We claim:

1. An antibody or antibody fragment with a binding affinity for the CD3 antigen, having a human constant region, a human or rat variable framework region, a heavy chain with CDRs having the amino acid sequences:
   (a) Ser-Phe-Pro-Met-Ala (SEQ ID NO:1),
   (b) Thr-Ile-Ser-Thr-Ser-Gly-Gly-Arg-Thr-Tyr-Tyr-Arg-Asp-Ser-Val-Lys-Gly (SEQ ID NO:2),
   (c) Phe-Arg-Gln-Tyr-Ser-Gly-Gly-Phe-Asp-Tyr (SEQ ID NO:3),
and a light chain with CDRs having the amino acid sequences:
   (d) Thr-Leu-Ser-Ser-Gly-Asn-Ile-Glu-Asn-Tyr-Val-His (SEQ ID NO:4),
   (e) Asp-Asp-Asp-Lys-Arg-Pro-Asp (SEQ ID NO:5),
   (f) His-Ser-Tyr-Val-Ser-Ser-Phe-Asn-Val (SEQ ID NO:6),
in which the heavy chain CDRs are arranged in the order (a), (b), (c) in the leader→constant region direction and the light chain CDRs are arranged in the order (d), (e), (f) in the leader→constant region direction.

2. An antibody or fragment thereof according to claim 1, having a heavy chain variable domain which comprises

```
Glu-Val-Gln-Leu-Leu-Glu-Ser-Gly-Gly-Gly-Leu-Val-Gln-Pro-Gly-Gly-    (SEQ ID NO:11)
Ser-Leu-Arg-Leu-Ser-Cys-Ala-Ala-Ser-Gly-Phe-Thr-Phe-Ser-Ser-Phe-
Pro-Met-Ala-Trp-Val-Arg-Gln-Ala-Pro-Gly-Lys-Gly-Leu-Glu-Trp-Val-
Ser-Thr-Ile-Ser-Thr-Ser-Gly-Gly-Arg-Thr-Tyr-Tyr-Arg-Asp-Ser-Val-
Lys-Gly-Arg-Phe-Thr-Ile-Ser-Arg-Asp-Asn-Ser-Lys-Asn-Thr-Leu-Tyr-
Leu-Gln-Met-Asn-Ser-Leu-Arg-Ala-Glu-Asp-Thr-Ala-Val-Tyr-Tyr-Cys-
Ala-Lys-Phe-Arg-Gln-Tyr-Ser-Gly-Gly-Phe-Asp-Tyr-Trp-Gly-Gln-Gly-
Thr-Leu-Val-Thr-Val-Ser-Ser.
```

3. An antibody or fragment thereof according to claim 1, having a light chain variable domain which comprises

```
Asp-Phe-Met-Leu-Thr-Gln-Pro-His-Ser-Val-Ser-Glu-Ser-Pro-Gly-Lys-    (SEQ ID NO:16)

Thr-Val-Ile-Ile-Ser-Cys-Thr-Leu-Ser-Ser-Gly-Asn-Ile-Glu-Asn-Asn-

Tyr-Val-His-Trp-Tyr-Gln-Gln-Arg-Pro-Gly-Arg-Ala-Pro-Thr-Thr-Val-

Ile-Phe-Asp-Asp-Lys-Arg-Pro-Asp-Gly-Val-Pro-Asp-Arg-Phe-Ser-

Gly-Ser-Ile-Asp-Arg-Ser-Ser-Asn-Ser-Ala-Ser-Leu-Thr-Ile-Ser-Gly-

Leu-Gln-Thr-Glu-Asp-Glu-Ala-Asp-Tyr-Tyr-Cys-His-Ser-Tyr-Val-Ser-

Ser-Phe-Asn-Val-Phe-Gly-Gly-Gly-Thr-Lys-Leu-Thr-Val-Leu.
```

4. An antibody or a fragment thereof according to claim 1, in which only one of the arms thereof has an affinity for the CD3 antigen.

5. An antibody or a fragment thereof according to claim 1, which is monovalent.

6. An antibody or a fragment according to claim 5, having only one Fab' arm.

7. A method of controlling graft rejection in a patient in need of such control, said method comprising the step of administering to said patient a therapeutically effective amount of an antibody or antibody fragment as claimed in claim 1.

* * * * *

UNITED STATES PATENT AND TRADEMARK OFFICE
CERTIFICATE OF CORRECTION

PATENT NO. : 5,968,509
DATED : October 19, 1999
INVENTOR(S) : GORMAN et al

It is certified that error appears in the above-identified patent and that said Letters Patent is hereby corrected as shown below:

On the title page item [73], delete "BTP International Limited" and replace by --BTG International Limited--.

Signed and Sealed this

Twenty-eighth Day of March, 2000

Attest:

Q. TODD DICKINSON

*Attesting Officer*  *Commissioner of Patents and Trademarks*

UNITED STATES PATENT AND TRADEMARK OFFICE

CERTIFICATE OF CORRECTION

PATENT NO. : 5,968,509
DATED : October 19, 1999
INVENTOR(S) : GORMAN et al

It is certified that error appears in the above-identified patent and that said letters patent is hereby corrected as shown below:

Abstract, line 11, insert -- Asn- -- after "Asn-". (second occurrence)

Column 34, line 30, (paragraph d), insert -- Asn- -- after "Asn-". (second occurrence)

Signed and Sealed this

Twenty-fourth Day of October, 2000

Attest:

Q. TODD DICKINSON

*Attesting Officer*  *Director of Patents and Trademarks*

SEQUENCE LISTING (1) GENERAL INFORMATION:

(iii) NUMBER OF SEQUENCES: 26

(2) INFORMATION FOR SEQ ID NO:1:

(i) SEQUENCE CHARACTERISTICS:
      (A) LENGTH: 5 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:1:

Ser Phe Pro Met Ala
    1               5

(2) INFORMATION FOR SEQ ID NO:2:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:2:

Thr Ile Ser Thr Ser Gly Gly Arg Thr Tyr Tyr Arg Asp Ser Val Lys
    1               5                   10                  15

Gly (2) INFORMATION FOR SEQ ID NO:3:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:3:

Phe Arg Gln Tyr Ser Gly Gly Phe Asp Tyr
    1               5                   10

(2) INFORMATION FOR SEQ ID NO:4:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:4:

Thr Leu Ser Ser Gly Asn Ile Glu Asn Asn Tyr Val His
    1               5                   10

(2) INFORMATION FOR SEQ ID NO:5:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

Asp Asp Asp Lys Arg Pro Asp
    1               5

(2) INFORMATION FOR SEQ ID NO:6:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:6:

His Ser Tyr Val Ser Ser Phe Asn Val
   1               5

(2) INFORMATION FOR SEQ ID NO:7:

(i) SEQUENCE CHARACTERISTICS:
       (A) LENGTH: 30 amino acids
       (B) TYPE: amino acid
       (C) STRANDEDNESS: double
       (D) TOPOLOGY: linear (ii) MOLECULE TYPE: peptide (xi) SEQUENCE DESCRIPTION: SEQ ID NO:7:

Glu Val Gln Leu Leu Glu Ser Gly Gly Gly Leu Val Gln Pro Gly Gly
   1               5                  10                  15

Ser Leu Arg Leu Ser Cys Ala Ala Ser Gly Phe Thr Phe Ser
               20                  25                  30

(2) INFORMATION FOR SEQ ID NO:8:

(i) SEQUENCE CHARACTERISTICS:
       (A) LENGTH: 14 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:8:

Trp Val Arg Gln Ala Pro Gly Lys Gly Leu Glu Trp Val Ser
   1               5                  10

(2) INFORMATION FOR SEQ ID NO:9:

(i) SEQUENCE CHARACTERISTICS:
       (A) LENGTH: 32 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:9:

Arg Phe Thr Ile Ser Arg Asp Asn Ser Lys Asn Thr Leu Tyr Leu Gln
   1               5                  10                  15

Met Asn Ser Leu Arg Ala Glu Asp Thr Ala Val Tyr Tyr Cys Ala Lys
               20                  25                  30

(2) INFORMATION FOR SEQ ID NO:10:

(i) SEQUENCE CHARACTERISTICS:
       (A) LENGTH: 11 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:10:

Trp Gly Gln Gly Thr Leu Val Thr Val Ser Ser
   1               5                  10

(2) INFORMATION FOR SEQ ID NO:11:

(i) SEQUENCE CHARACTERISTICS:
    (A) LENGTH: 119 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:11:

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Pro Met Ala Trp Val Arg Gln Ala Pro Gly Lys Gly Leu Glu Trp Val
        35                  40                  45

Ser Thr Ile Ser Thr Ser Gly Gly Arg Thr Tyr Tyr Arg Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Phe Arg Gln Tyr Ser Gly Gly Phe Asp Tyr Trp Gly Gln Gly
            100                 105                 110

Thr Leu Val Thr Val Ser Ser
        115

(2) INFORMATION FOR SEQ ID NO:12:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:12:

Asp Phe Met Leu Thr Gln Pro His Ser Val Ser Glu Ser Pro Gly Lys
    1               5                   10                  15

Thr Val Ile Ile Ser Cys
                20

(2) INFORMATION FOR SEQ ID NO:13:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:13:

Trp Tyr Gln Gln Arg Pro Gly Arg Ala Pro Thr Thr Val Ile Phe
    1               5                   10                  15

(2) INFORMATION FOR SEQ ID NO:14:

(i) SEQUENCE CHARACTERISTICS:
        (A) LENGTH: 34 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:14:

Gly Val Pro Asp Arg Phe Ser Gly Ser Ile Asp Arg Ser Ser Asn Ser
1               5                   10                  15

Ala Ser Leu Thr Ile Ser Gly Leu Gln Thr Glu Asp Glu Ala Asp Tyr
            20                  25                  30

Tyr Cys (2) INFORMATION FOR SEQ ID NO:15:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:15:

Phe Gly Gly Gly Thr Lys Leu Thr Val Leu
1               5                   10

(2) INFORMATION FOR SEQ ID NO:16:

(i) SEQUENCE CHARACTERISTICS:
        (A) LENGTH: 110 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:16:

Asp Phe Met Leu Thr Gln Pro His Ser Val Ser Glu Ser Pro Gly Lys
1               5                   10                  15

Thr Val Ile Ile Ser Cys Thr Leu Ser Ser Gly Asn Ile Glu Asn Asn
            20                  25                  30

Tyr Val His Trp Tyr Gln Gln Arg Pro Gly Arg Ala Pro Thr Thr Val
            35                  40                  45

Ile Phe Asp Asp Asp Lys Arg Pro Asp Gly Val Pro Asp Arg Phe Ser
50                  55                  60

Gly Ser Ile Asp Arg Ser Ser Asn Ser Ala Ser Leu Thr Ile Ser Gly
65                  70                  75                  80

Leu Gln Thr Glu Asp Glu Ala Asp Tyr Tyr Cys His Ser Tyr Val Ser
                85                  90                  95

Ser Phe Asn Val Phe Gly Gly Gly Thr Lys Leu Thr Val Leu
                100                 105                 110

(2) INFORMATION FOR SEQ ID NO:17:

(i) SEQUENCE CHARACTERISTICS:
        (A) LENGTH: 15 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:17:

AGCTTTCCAA TGGCC                                                          15

(2) INFORMATION FOR SEQ ID NO:18:

(i) SEQUENCE CHARACTERISTICS:

(A) LENGTH: 51 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:18:

ACCATTAGTA CTAGTGGTGG TAGAACTTAC TATCGAGACT CCGTGAAGGG C            51

(2) INFORMATION FOR SEQ ID NO:19:

(i) SEQUENCE CHARACTERISTICS:
        (A) LENGTH: 30 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:19:

TTTCGGCAGT ACAGTGGTGG CTTTGATTAC                                    30

(2) INFORMATION FOR SEQ ID NO:20:

(i) SEQUENCE CHARACTERISTICS:
        (A) LENGTH: 39 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:20:

ACACTCAGCT CTGGTAACAT AGAAAACAAC TATGTGCAC                          39

(2) INFORMATION FOR SEQ ID NO:21:

(i) SEQUENCE CHARACTERISTICS:
        (A) LENGTH: 21 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:21:

GATGATGATA AGAGACCGGA T                                             21

(2) INFORMATION FOR SEQ ID NO:22:

(i) SEQUENCE CHARACTERISTICS:
        (A) LENGTH: 27 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:22:

CATTCTTATG TTAGTAGTTT TAATGTT                                       27

(2) INFORMATION FOR SEQ ID NO:23:

(i) SEQUENCE CHARACTERISTICS:
        (A) LENGTH: 357 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:23:

```
GAGGTCCAAC TGCTGGAGTC TGGGGGCGGT TTAGTGCAGC CTGGAGGGTC CCTGAGACTC      60

TCCTGTGCAG CCTCAGGATT CACTTTCAGT AGCTTTCCAA TGGCCTGGGT CCGCCAGGCT     120

CCAGGGAAGG GTCTGGAGTG GGTCTCAACC ATTAGTACTA GTGGTGGTAG AACTTACTAT     180

CGAGACTCCG TGAAGGGCCG ATTCACTATC TCCAGAGATA ATAGCAAAAA TACCCTATAC     240

CTGCAAATGA ATAGTCTGAG GGCTGAGGAC ACGGCCGTCT ATTACTGTGC AAAATTTCGG     300

CAGTACAGTG GTGGCTTTGA TTACTGGGGC CAAGGGACCC TGGTCACCGT CTCCTCA       357
```

(2) INFORMATION FOR SEQ ID NO:24:

(i) SEQUENCE CHARACTERISTICS:
       (A) LENGTH: 330 base pairs
       (B) TYPE: nucleic acid
       (C) STRANDEDNESS: double
       (D) TOPOLOGY: linear (ii) MOLECULE TYPE: DNA (genomic)

(xi) SEQUENCE DESCRIPTION: SEQ ID NO:24:

```
GACTTCATGC TGACTCAGCC CCACTCTGTG TCTGAGTCTC CCGGAAAGAC AGTCATTATT      60

TCTTGCACAC TCAGCTCTGG TAACATAGAA AACAACTATG TGCACTGGTA CCAGCAAAGG     120

CCGGGAAGAG CTCCCACCAC TGTGATTTTC GATGATGATA AGAGACCGGA TGGTGTCCCT     180

GACAGGTTCT CTGGCTCCAT TGACAGGTCT TCCAACTCAG CCTCCCTGAC AATCAGTGGT     240

CTGCAAACTG AAGATGAAGC TGACTACTAC TGTCATTCTT ATGTTAGTAG TTTTAATGTT     300

TTCGGCGGTG GAACAAAGCT CACTGTCCTT                                      330
```

(2) INFORMATION FOR SEQ ID NO:25:

(i) SEQUENCE CHARACTERISTICS:
       (A) LENGTH: 119 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:25:

```
Gln Val Gln Leu Gln Glu Ser Gly Gly Gly Leu Val Gln Pro Gly Arg
  1               5                  10                  15

Ser Met Lys Leu Ser Cys Ala Ala Ser Gly Phe Thr Phe Ser Ser Phe
             20                  25                  30

Pro Met Ala Trp Val Arg Gln Ala Pro Lys Lys Gly Leu Glu Trp Val
         35                  40                  45

Ala Thr Ile Ser Thr Ser Gly Gly Arg Thr Tyr Tyr Arg Asp Ser Val
     50                  55                  60

Lys Gly Arg Phe Thr Ile Ser Arg Asp Asn Gly Lys Ser Ile Leu Tyr
 65                  70                  75                  80

Leu Gln Met Asn Ser Leu Arg Ser Glu Asp Thr Ala Thr Tyr Tyr Cys
                 85                  90                  95

Ser Arg Phe Arg Gln Tyr Ser Gly Gly Phe Asp Tyr Trp Gly Gln Gly
             100                 105                 110

Thr Thr Val Thr Val Ser Ser
             115
```

(2) INFORMATION FOR SEQ ID NO:26:

(i) SEQUENCE CHARACTERISTICS:
    (A) LENGTH: 110 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:26:

```
Gln Ala Val Val Thr Gln Ala Asn Ser Val Ser Thr Ser Leu Gly Ser
1               5                   10                  15

Thr Val Lys Leu Ser Cys Thr Leu Ser Ser Gly Asn Ile Glu Asn Asn
            20                  25                  30

Tyr Val His Trp Tyr Gln Leu Tyr Glu Gly Arg Ser Pro Thr Thr Met
        35                  40                  45

Ile Tyr Asp Asp Asp Lys Arg Pro Asp Gly Val Pro Asp Arg Phe Ser
    50                  55                  60

Gly Ser Ile Asp Arg Ser Ser Asn Ser Ala Phe Leu Thr Ile His Asn
65                  70                  75                  80

Val Ala Ile Glu Asp Glu Ala Ile Tyr Phe Cys His Ser Tyr Val Ser
            85                  90                  95

Ser Phe Asn Val Phe Gly Gly Gly Thr Lys Leu Thr Val Leu
            100                 105                 110
```